United States Patent
Gray et al.

(10) Patent No.: US 7,052,858 B2
(45) Date of Patent: May 30, 2006

(54) DIAGNOSTIC ASSAYS FOR DETECTION OF CRYPTOSPORIDIUM PARVUM

(75) Inventors: Jeff Gray, Solano Beach, CA (US);
Gunars E. Valkirs, Escondido, CA (US); Kent Buechler, Carlsbad, CA (US)

(73) Assignee: BIOSITE Incorporated, San Diego, CA (US)

( * ) Notice: Subject to any disclaimer, the term of this patent is extended or adjusted under 35 U.S.C. 154(b) by 0 days.

(21) Appl. No.: 09/877,933

(22) Filed: Jun. 7, 2001

(65) Prior Publication Data
US 2004/0096454 A1 May 20, 2004

Related U.S. Application Data

(62) Division of application No. 09/158,180, filed on Sep. 21, 1998, now abandoned.

(51) Int. Cl.
- G01N 33/53 (2006.01)
- G01N 33/567 (2006.01)
- G01N 33/537 (2006.01)
- G01N 33/543 (2006.01)
- C12M 1/36 (2006.01)

(52) U.S. Cl. .............. 435/7.22; 435/7.1; 435/7.2; 435/7.21; 435/7.92; 435/7.94; 435/34; 435/174; 435/243; 435/283.1; 435/286.3; 435/287.7; 435/287.9; 435/288.3; 436/501; 436/512; 436/513; 436/518; 436/807; 436/808; 436/810

(58) Field of Classification Search ............. 435/7.1, 435/7.2, 7.21, 7.22, 7.92, 7.93, 7.94, 7.95, 435/34, 173, 243, 342, 174, 283.1, 286.3, 435/287.7, 287.9, 288.3; 530/388.6; 930/210; 436/501, 512, 513, 518, 807, 808, 810
See application file for complete search history.

(56) References Cited

U.S. PATENT DOCUMENTS

| | | |
|---|---|---|
| 4,200,690 A | 4/1980 | Root et al. |
| 5,633,141 A | 5/1997 | Lee et al. |
| 5,700,659 A | 12/1997 | Yamada et al. |
| 5,700,678 A | 12/1997 | Toyoshima et al. |
| 5,798,249 A * | 8/1998 | Braxton et al. ............. 435/233 |

FOREIGN PATENT DOCUMENTS

WO  WO 93/24649  12/1993

OTHER PUBLICATIONS

Anusz et al. 1990. J. of Clinical Microbiology. vol. 28 (12): 2770-2774.*
Blunt et al. 1996. Gene. pp. 221-223.*
Anusz et al. (1990) *J. of Clin. Micro.* 28: 2770-2774.
Arrowood et al. (1989) *Infect Immun.* 57: 2283-2288.

(Continued)

Primary Examiner—Lynette R. F. Smith
Assistant Examiner—Ja-Na Hines
(74) Attorney, Agent, or Firm—Townsend & Townsend & Crew LLP; Nathan S. Cassell

(57) ABSTRACT

This invention provides a novel *Cryptosporidium parvum* protein disulfide isomerase polypeptide, and nucleic acids that encode this polypeptide. The invention also provides methods, reagents, and kits that are useful for diagnosing infection by *Cryptosporidium parvum*. The methods are based on the discovery of binding agents, including recombinant polyclonal antibodies, that bind to the protein disulfide isomerase polypeptide of *C. parvum*.

16 Claims, 4 Drawing Sheets

OTHER PUBLICATIONS

Bjorneby et al. (1990) *J. Immunol.* 145: 298-304.
Bjorneby et al. (1991) *Infect. Immun.* 59: 1172-1176.
Blunt et al. (1996) *Gene* 181: 221-223.
Current et al. (1983) *N.Engl. J. Med.* 1252-1257.
Goldstein et al., "Cryptosporidiosis: An Outbreak Associated with Drinking Wate Despite State-of-the-Art Water Tretment," (Mar. 1, 1996) *Annals of Internal Medicine.*
Khramtsov et al. (1997) *Biochemical and Biophysical Research Communications* 230: 164-166.
Lumb et al. (1989) *Immunol. Cell Biol.* 67: 267-270.
Mead et al. (1988) *J. Parasitol.* 74: 135-143.
Perryman et al. (1990) *Infect. Immun.* 58: 257-259.
Peterson et al. (1992) *Infect. Immun.* 60(6): 2343-2348.
Peterson et al. (1992) *Infect. Immun.* 60(12):5132-5138.
Pitlik et al. (1983) *Arch. Intern. Med.* 143: 2269-2275.
Riggs et al. (1989) *J. Immunol.* 143: 1340-1345.
Soave et al. (1984) *Ann. Intern. Med.* 100: 504-511.
Tilley et al. (1991) *Infect. Immun.*59(3): 1002-1007.
Tilley et al. (1990) *Can. J. Zool.* 68: 1513-1519.
Tilley et al. (1994) *FEMS Microbiology Letters* 120: 275-278.
Wolfson et al. (1985) *N. Engl. J. Med.* 312: 1278-1282.
"Cryptosporidium Ag," Cypress Diagnostics, Technical Sheet Ref. HP008, rev. Sep. 1995.
"ProSpecT Cryptosporidium Microplate Assay" Package Insert (1998) Alexon-Trend, Inc., Ramsey, MN.
Hassan et al., "Detection of Cryptosporidium Antigen in Stool Samples Among Diarrhoeic Children," J. Egypt. Soc. of Parasitol, 25(3) 599-606.

* cited by examiner

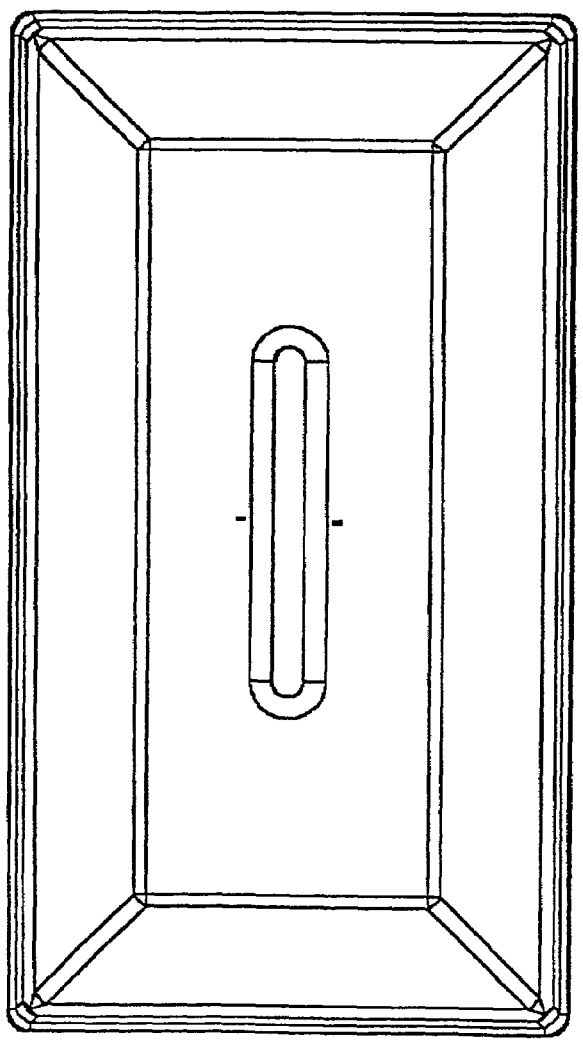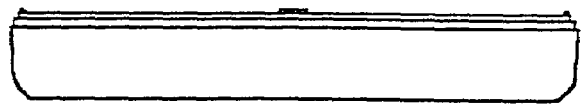

Figure 3A

Nucleotide sequence of *Cryptosporidium parvum* protein disulfide isomerase cDNA

```
001  atgatcggaa ttagaagctt ggtttcagca gcatttttag gtttttcttg tctctccaag
061  gtagtcttgg gtgagatga agctcacttc atttcagaac acattacttc cttaacttcc
121  tccaacttcg aagacttcat taagagcaag gaacacgtaa ttgttacttt ctttgcccca
181  tggtgcggcc attgtactgc tttagagcca gaattcaagg caacatgcgc tgaaatctca
241  aagctctctc cccagtaca ctgtggcagt gttgatgcaa ctgaaaatat ggagcttgca
301  caacaatatg gtgtgagcgg ataccccaacc atcaaattct tcagtggtat tgacagtgtt
361  cagaactatt caggagcaag aagcaaggat gcattcatca agtatattaa gaagttgacc
421  ggaccagcag tccaagttgc tgaatcagaa gaagctatca agacaatctt cgcttcttct
481  tcttcagcct ttgttggaag attcacctct aaggactcag ctgagtatgc tgtcttcgag
541  aaggttgcta gtggtcaccg cgagcacaac tatgctttca ttgctttctt ccaagaaggt
601  gaacaaaagc tcgaggtatt acacaaggac gaggagccag tttctctccc aatgccaaag
661  actgttgaag agttggagga caagatatcc ataatgaatg tactcttgtt ctctgcaatt
721  agtgctgaga actactccct ctatatgtca agagaaggtt atactgcctg ttctgtggta
782  ctaacgagga cttcgccaag tatgcttcaa acattagaaa ggttgcagct gattacagag
842  aaaagtatgc ctttgttttc  cttgatact gagcaatttg gttcccatgc tactcaacat
901  ctcttaattg agaaattccc aggtttggtt atccaaagtg tcaatgttcc atcaattaga
961  tacatgtatg gtccagctaa attcgactct gttgagccat taaaggaatt tatgaagcaa
1021 gttctgaagg gcaagcacga actcagcagc aagtctgagc caatcccagc tgagcaatct
1081 ggtccagtca ctgttgttgt tggtaagacc ttcgaagaaa ttgtttttcag aagtgacaag
1141 gatgttcttt tggaaatcta tgcccaatgg tgtggacact gtaagaacct cgagccaatc
1201 tacaaccaac tcggcgaaga gtacaaggac aacgacaagg ttgtgattgc aaagatcaat
1261 ggaccacaaa acgatatccc atatgaaggt ttcagtccaa gagccttccc aactatcttg
1321 ttcgtcaagg ccggaactag aacccccaatt ccttatgatg gaaagagaac tgtttgaggcc
1381 ttcaaggaat tcatcagtga acattcttcc ttccctcaag aaaaggaatc tcgtgacgaa
1441 ctctaa
```

Figure 3B

Deduced Amino Acid Sequence of *C. parvum* Protein Disulfide Isomerase

1 MIGIRSLVSAAFLGFSCLSKVVLGGDEAHFISEHITSLTSSNFEDFIKSKEHVIVTFFAP
   61 WCGHCTALEPEFKATCAEISKLSPPVHCGSVDATENMELAQQYGVSGYPTIKFFSGIDSV
  121 QNYSGARSKDAFIKYIKKLTGPAVQVAESEEAIKTIFASSSSAFVGRFTSKDSAEYAVFE
  181 KVASGHREHNYAFIAFFQEGEQKLEVLHKDEEPVSLPMPKTVEELEAKISIMNVPLFSAI
  241 SAENYSLYMSREGYTAWFCGTNEDFAKYASNIRKVAADYREKYAFVFLDTEQFGSHATQH
  301 LLIEKFPGLVIQSVNVPSIRYMYGPAKFDSVEPLKEFMKQVSEGKHELSIKSEPIPAEQS
  361 GPVTVVVGKTFEEIVFRSDKDVLLEIYAQWCGHCKNLEPIYNQLGEEYKDNDKVVIAKIN
  421 GPQNDIPYEGFSPRAFPTILFVKAGTRTPPYDGKRTVEAFKEFISEHSSFPQEKESRDEL

DIAGNOSTIC ASSAYS FOR DETECTION OF CRYPTOSPORIDIUM PARVUM

CROSS-REFERENCE TO RELATED APPLICATIONS

This application is a divisional of, and claims the benefit of priority from, U.S. patent application Ser. No. 09/158,180, filed Sep. 21, 1998 (now abandoned), the full disclosure of which is incorporated herein by reference in its entirety.

STATEMENT REGARDING FEDERALLY SPONSORED RESEARCH

This invention was made with government support under Grant No. 4 R44 AI40801-02, awarded by the National Institute of Allergy and Infectious Diseases. The Government has certain rights in the invention.

BACKGROUND OF THE INVENTION

1. Field of the Invention

This invention pertains to the field of diagnostic assays for detecting infection of an animal by the protozoan parasite *Cryptosporidium*, in particular, *C. parvum*. Also provided are novel *C. parvum* protein disulfide isomerase (PDI) polypeptides, and nucleic acids encoding the polypeptides.

2. Background

The *Cryptosporidium* parasites cause infection of a wide variety of animals, including birds, reptiles, and mammals. *C. parvum* is the principal pathogenic *Cryptosporidium* species in humans and domestic animals. *C. parvum* can cause acute diarrhea in hosts, although in immunocompetent hosts the disease is self-limiting (Wolfson et al. (1985) *N. Engl. J. Med.* 312: 1278–1282). In immunocompromised hosts (e.g., AIDS patients), *C. parvum* can cause a severe and potential lethal disease (Current et al. (1983) *N. Engl. J. Med.* 1252–1257; Pitlik et al. (1983) *Arch. Intern. Med.* 143: 2269–2275; Soave et al. (1984) *Ann. Intern. Med.* 100: 504–511).

*Cryptosporidium* infection typically results from ingestion of oocysts, which become excystated and release sporozoites. The sporozoites then infect gut epithelial cells. Once in the epithelial cells, the sporozoites mature into merozoites, which are released and infect additional epithelial cells. *Cryptosporidium* also has a sexual cycle, which also occurs in the gut epithelial cells and involves the production of sporulated oocysts. Some of the oocysts can become excysted before being shed from the cell. Both sporozoites and merozoites are found free in the gut.

Several *Cryptosporidium* sporozoite and merozoite surface antigen polypeptides have been reported. For example, five *C. parvum* surface antigens, genes encoding the antigens, and the production of antibodies against *C. parvum* are discussed in Peterson et al. (1992) *Infect. Immun.* 60: 2343–2348 and PCT patent application PCT/US93/05460 (International Publication No. WO 93/24649). Additional *Cryptosporidium* surface antigens, and production of anti-*Cryptosporidium* antibodies are discussed in, for example, Arrowood et al. (1989) *Infect. Immun.* 57: 2283–2288; Bjorneby et al. (1991) *Infect. Immun.* 59: 1172–1176; Bjorneby et al. (1990) *J. Immunol.* 145: 298–304; Lumb et al. (1989) *Immunol. Cell Biol.* 67: 267–270; Mead et al. (1988) *J. Parasitol.* 74: 135–143; Perryman et al. (1990) *Infect. Immun.* 58: 257–259; Riggs et al. (1989) *J. Immunol.* 143: 143: 1340–1345; Tilley et al. (1991) *Infect. Immun.* 59: 1002–1007; and Tilley et al. (1990) *Can. J. Zool.* 68: 1513–1519.

Diagnosis of *Cryptosporidium* infection has traditionally involved microscopic detection of ova and parasites (O&P) in stools, which is a laborious process. Other assays have used stains or fluorescent-labeled antibodies which are contacted with a sample, which is then examined under a microscope. Both of these assays, however, require subjective interpretation of results. More recently, antigen capture enzyme immunoassays have been described (e.g., Cypress Diagnostics "*Cryptosporidium* Ag"; Alexon ProSpecT *Cryptosporidium* Microplate Assay).

Therefore, a need exists for improved methods for detecting *Cryptosporidium* infection in animals, including humans. The present invention fulfills this and other needs.

SUMMARY OF THE INVENTION

The present invention provides a novel protein disulfide isomerase (PDI) polypeptide from *Cryptosporidium parvum*, and nucleic acids that encode the novel PDI. The PDI polypeptides of the invention include an amino acid sequence of at least ten consecutive amino acids that are at least substantially identical to a subsequence of an amino acid sequence as set forth in SEQ ID NO: 3.

The isolated PDI nucleic acids of the invention include a polynucleotide sequence that encodes an amino acid sequence of which at least ten consecutive amino acids that are at least substantially identical to a subsequence of an amino acid sequence as set forth in SEQ ID NO: 3.

In another embodiment, the invention provides methods of diagnosing infection of a mammal by a *Cryptosporidium* species, in particular *C. parvum*. The methods involve contacting a stool sample obtained from the mammal with a capture reagent that binds to a protein disulfide isomerase (PDI) of *C. parvum*. The capture reagent forms a complex with the PDI if PDI is present in the test sample. The presence or absence of the PDI bound to the capture reagent is then detected; the presence of the PDI is indicative of *Cryptosporidium* infection of the mammal.

The invention also provides devices and kits for diagnosing infection of a mammal by a *Cryptosporidium* species, in particular *C. parvum*. The kits typically include, inter alia, a solid support upon which is immobilized a capture reagent which binds to a PDI of *C. parvum*, and a detection reagent which binds to the PDI.

Also provided by the invention are recombinant monoclonal and polyclonal antibodies that bind to *C. parvum* PDI.

BRIEF DESCRIPTION OF THE DRAWINGS

FIG. 1A-C show a top piece of an apparatus for performing an immunoassay for detecting *C. parvum* infection in a sample. FIG. 1A is a top view, showing an elongated well in the center. FIG. 1B is a section view of the top piece, showing a membrane that is ultrasonically welded to the underside of the top piece. FIG. 1C is an end view of the top piece of the apparatus.

FIG. 2A is a top view, FIG. 2B is a section view, and FIG. 2C is an end view of the bottom piece. To construct a complete apparatus, a bottom piece is joined to a top piece such as is shown in FIGS. 1A–C.

FIG. 3A presents the nucleotide sequence of a *Cryptosporidium parvum* protein disulfide isomerase (PDI) cDNA (SEQ ID NO: 1). The sequence differs from a PDI nucleotide sequence reported by Blunt et al. ((1996) *Gene* 181: 221–223) in two locations. First, the sequence described herein includes a guanine residue at position 766 (bold) that is not present in the Blunt et al. sequence. Second, the sequence described herein is lacking a cytosine after position 860 (shown as a bolded underline). FIG. 3B shows the deduced amino acid sequence of the *C. parvum* PDI (SEQ ID NO: 2). A 32 amino acid region of the amino acid sequence (shown in bold) differs from the amino acid sequence for PDI reported by Blunt et al., supra.

DETAILED DESCRIPTION

Definitions

Figure 2A:
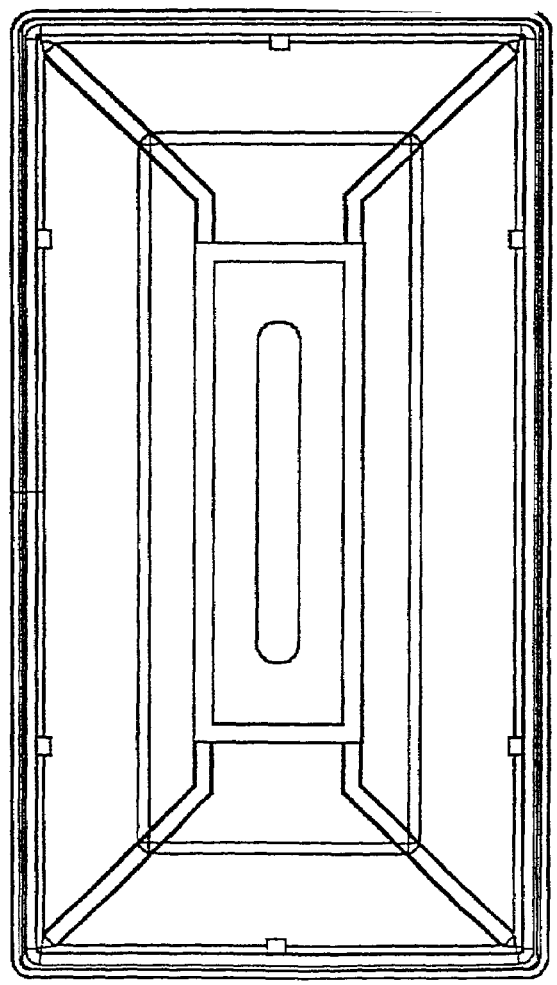
FIG. 2A-C show a bottom piece of an apparatus for performing an immunoassay for detecting *C. parvum* infection in a sample.

The phrases "specifically binds to" or "specifically immunoreactive with", when referring to an antibody or other binding moiety refers to a binding reaction which is determinative of the presence of a target antigen in the presence of a heterogeneous population of proteins and other biologics. Thus, under designated assay conditions, the specified binding moieties bind preferentially to a particular target antigen and do not bind in a significant amount to other components present in a test sample. Specific binding to a target antigen under such conditions may require a binding moiety that is selected for its specificity for a particular target antigen. A variety of immunoassay formats may be used to select antibodies that are specifically immunoreactive with a particular protein. For example, solid-phase ELISA immunoassays are routinely used to select monoclonal antibodies specifically immunoreactive with an antigen. See Harlow and Lane (1988) *Antibodies, A Laboratory Manual*, Cold Spring Harbor Publications, New York, for a description of immunoassay formats and conditions that can be used to determine specific immunoreactivity. Typically a specific or selective reaction will be at least twice background signal or noise and more typically more than 10 to 100 times background. Specific binding between an antibody or other binding agent and an antigen means a binding affinity of at least $10^6$ $M^{-1}$. Preferred binding agents bind with affinities of at least about $10^7$ $M^{-1}$, and preferably $10^8$ $M^{-1}$ to $10^9$ $M^{-1}$ or $10^{10}$ $M^{-1}$.

The term "epitope" means an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The basic antibody structural unit is known to comprise a tetramer. Each tetramer is composed of two identical pairs of polypeptide chains, each pair having one "light" (about 25 kDa) and one "heavy" chain (about 50–70 Kda). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (See, e.g., Paul, *Fundamental Immunology*, 3$^{rd}$ Ed., 1993, Raven Press, New York).

The variable regions of each light/heavy chain pair form the antibody binding site. The chains all exhibit the same general structure of relatively conserved framework regions (FR) joined by three hypervariable regions, also called complementarily determining regions or CDRs. The CDRs from the two chains of each pair are aligned by the framework regions, enabling binding to a specific epitope. CDR and FR residues are delineated according to the standard sequence definition of Kabat et al., supra. An alternative structural definition has been proposed by Chothia et al. (1987) *J. Mol. Biol.* 196: 901–917; (1989) *Nature* 342: 878–883; and (1989) *J. Mol. Biol.* 186: 651–663.

The term "antibody" is used to mean whole antibodies and binding fragments thereof. Binding fragments include single chain fragments, Fv fragments and Fab fragments The term Fab fragment is sometimes used in the art to mean the binding fragment resulting from papain cleavage of an intact antibody. The terms Fab' and F(ab')$_2$ are sometimes used in the art to refer to binding fragments of intact antibodies generated by pepsin cleavage. Here, "Fab" is used to refer generically to double chain binding fragments of intact antibodies having at least substantially complete light and heavy chain variable domains sufficient for antigen-specific bindings, and parts of the light and heavy chain constant regions sufficient to maintain association of the light and heavy chains. Usually, Fab fragments are formed by complexing a full-length or substantially full-length light chain with a heavy chain comprising the variable domain and at least the CH1 domain of the constant region.

An isolated species or population of species means an object species (e.g., binding polypeptides of the invention) that is the predominant species present (i.e., on a molar basis it is more abundant than other species in the composition). Preferably, an isolated species comprises at least about 50, 80 or 90 percent (on a molar basis) of all macromolecular species present. Most preferably, the object species is purified to essential homogeneity (contaminant species cannot be detected in the composition by conventional detection methods).

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids, refers to two or more sequences or subsequences that have at least 80%, preferably 85%, most preferably 90–95% nucleotide identity, when compared and aligned for maximum correspondence, as measured using one of the following sequence comparison algorithms or by visual inspection. For amino acid sequences, "substantial identical" refers to two or more sequences or subsequences that have at least 60% identity, preferably 75% identity, and more preferably 90–95% identify, when compared and aligned for maximum correspondence, as measured using one of the following sequence comparison algorithms or by visual inspection. Preferably, the substantial identity exists over a region of the nucleic acid or amino acid sequences that is at least about 10 residues in length, more preferably over a region of at least about 20 residues, and most preferably the sequences are substantially identical over at least about 100 residues. In a most preferred embodiment, the sequences are substantially identical over the entire length of the specified regions (e.g., coding regions).

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403–410 and Altschuel et al. (1977) *Nucleic Acids Res.* 25: 3389–3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following five groups each contain amino acids that are conservative substitutions for one another:

| | |
|---|---|
| Aliphatic: | Glycine (G), Alanine (A), Valine (V), Leucine (L), Isoleucine (I); |
| Aromatic: | Phenylalanine (F), Tyrosine (Y), Tryptophan (W); |
| Hydroxy: | Serine (S), Threonine (T); |
| Sulfur-containing: | Methionine (M), Cysteine (C); |
| Basic: | Arginine (R), Lysine (K), Histidine (H); |
| Acidic: | Aspartic acid (D), Glutamic acid (E); |
| Amide: | Asparagine (N), Glutamine (Q). |

See also, Creighton (1984) *Proteins*, W.H. Freeman and Company. In addition, individual substitutions, deletions or additions which alter, add or delete a single amino acid or a small percentage of amino acids in an encoded sequence are also "conservatively modified variations".

DESCRIPTION OF THE PREFERRED EMBODIMENTS

The invention provides novel *Cryptosporidium parvum* protein disulfide isomerase (PDI) polypeptides, and nucleic acids that encode these polypeptides. Also provided by the invention are methods, reagents, and kits that are useful for diagnosing infection of a mammal by a *Cryptosporidium* species, in particular *C. parvum*. The assays provide a rapid, accurate and cost-effective means for detecting *Cryptosporidium* infection. The methods of the invention are both sensitive and specific, and can be used for detecting a *Cryptosporidium* antigen that is soluble.

The methods, compositions and kits provided by the instant invention are useful for detecting *Cryptosporidium* infection in test samples, including biological samples such as cultures, tissue samples, bodily fluids, and the like. Typically, the biological sample analyzed for *Cryptosporidium* infection will be a stool sample. For liquid or semi-solid stool samples, a portion of the sample is added to an assay container and, optionally, diluted with a suitable diluent such as water or an appropriate buffer and mixed. Suitable buffers include, for example, buffered protein solutions and the like. Solid stool samples can be placed in a diluent and suspended by vigorous mixing. Typically, the sample is diluted sufficiently to provide a solution of suitable clarity for use in the assays; this is generally about a 3–20 fold dilution, with about a 10-fold dilution being typical. After mixing, one can clarify the sample by, for example, filtration or centrifugation or other methods known to those of skill in the art. In general, well known methods for preparing test samples for assays, such as immunoassays, are suitable for preparing test samples for analysis using the methods provided by the invention.

A. *C. parvum* Protein Disulfide Isomerase (PDI) Nucleic Acids and Polypeptides

The invention provides novel isolated PDI polypeptides, and isolated nucleic acids that encode the PDI polypeptides.

1. *C. parvum* Protein Disulfide Isomerase Polypeptides

The present invention provides novel *C. parvum* protein disulfide isomerase (PDI) polypeptides. The polypeptides are useful for several purposes. For example, one can use the PDI polypeptides of the invention to facilitate the folding of disulfide-containing proteins, e.g., proteins produced using recombinant methods. The polypeptides are also useful as immunogens for producing antibodies against PDI; such antibodies find use in immunoassays, for purification of PDI, and other uses.

The PDI polypeptides of the invention have many uses, including use as immunogens for producing antibodies against PDI. The nucleic acids of the invention find use for recombinant expression of PDI, for identifying protein disulfide isomerases from other species, and for other purposes known to those of skill in the art.

The amino acid sequence of a *C. parvum* PDI polypeptide of the invention is shown in FIG. 3. The amino acid sequence of the PDI polypeptides of the invention differ substantially from a *C. parvum* PDI predicted amino acid sequence that had been reported previously (Blunt et al. (1996) *Gene* 181: 221–223; Genbank Accession No. U48261). Specifically, a 32 amino acid region of the PDI sequence of the present invention is completely different from that of Blunt et al., as shown below. The 32 amino acid region that differs between the two sequences is highlighted in bold type, and the numbering at the beginning and ending of the sequence corresponds to the numbering convention used by Blunt et al.

```
Applicants     250 SREGYTAWFCGTNEDFAKYASNIRKVAADYREKYAFVFLDT 290 (SEQ ID NO: 5)

Blunt et al.   250 SREGYTPGSVVLTRTSPSMLQTLERLQLITEKSMPLFSLDT 290 (SEQ ID NO: 4)
```

Accordingly, the present invention provides isolated protein disulfide isomerase polypeptides that include an amino acid sequence of which at least ten consecutive amino acids are at least substantially identical to a subsequence of the amino acid sequence AWFCGTNEDFAKYAS-NIRKVAADYR EKYAFVF (SEQ ID NO: 3). More preferably, the PDI polypeptides of the invention include at least 15, more preferably at least 20, still more preferably at least about 25–32 amino acids that are substantially identical to the amino acid sequence set forth in SEQ ID NO: 3. In a particularly preferred embodiment, the PDI polypeptides of the invention include an amino acid sequence that is identical to the amino acid sequence of SEQ ID NO: 3, or a subsequence thereof.

Included in the invention are isolated PDI polypeptides that are at least substantially identical to a PDI polypeptide having an amino acid sequence as set forth in SEQ ID NO: 2, which provides the full-length PDI polypeptide.

The PDI polypeptides of the invention can be produced by methods known to those of skill in the art. In a preferred embodiment, the PDI proteins or subsequences thereof are synthesized using recombinant DNA methodology. Generally this involves creating a DNA sequence that encodes the polypeptide, modified as desired, placing the DNA in an expression cassette under the control of a particular promoter, expressing the protein in a host, isolating the expressed protein and, if required, renaturing the protein.

The polypeptides of the invention can be expressed in a variety of host cells, including *E. coli*, other bacterial hosts, yeasts, filamentous fungi, and various higher eukaryotic cells such as the COS, CHO and HeLa cells lines and myeloma cell lines. Techniques for gene expression in microorganisms are described in, for example, Smith, *Gene Expression in Recombinant Microorganisms* (*Bioprocess Technology*, Vol. 22), Marcel Dekker, 1994. Examples of bacteria that are useful for expression include, but are not limited to, *Escherichia, Enterobacter, Azotobacter, Erwinia, Bacillus, Pseudomonas, Klebsielia, Proteus, Salmonella, Serratia, Shigella, Rhizobia, Vitreoscilla*, and *Paracoccus*. Filamentous fungi that are useful as expression hosts include, for example, the following genera: *Aspergillus, Trichoderma, Neurospora, Penicillium, Cephalosporium, Achlya, Podospora, Mucor, Cochliobolus*, and *Pyricularia*. See, e.g., U.S. Pat. No. 5,679,543 and Stahl and Tudzynski, Eds., *Molecular Biology in Filamentous Fungi*, John Wiley & Sons, 1992. Synthesis of heterologous proteins in yeast is well known and described in the literature. *Methods in Yeast Genetics*, Sherman, F., et al., Cold Spring Harbor Laboratory, (1982) is a well recognized work describing the various methods available to produce the enzymes in yeast.

A polynucleotide that encodes a PDI polypeptide of the invention can be operably linked to appropriate expression control sequences for a particular host cell in which the polypeptide is to be expressed. Such constructs are often referred to as "expression cassettes." For *E. coli*, appropriate control sequences include a promoter such as the T7, trp, or lambda promoters, a ribosome binding site and preferably a transcription termination signal. For eukaryotic cells, the control sequences typically include a promoter which optionally includes an enhancer derived from immunoglobulin genes, SV40, cytomegalovirus, etc., and a polyadenylation sequence, and may include splice donor and acceptor sequences. In yeast, convenient promoters include GAL1,10 (Johnson and Davies (1984) *Mol. Cell. Biol.* 4:1440–1448) ADH2 (Russell et al. (1983) *J. Biol. Chem.* 258:2674–2682), PHO5 (*EMBO J.* (1982) 6:675–680), and MFα1 (Herskowitz and Oshima (1982) in *The Molecular Biology of the Yeast Saccharomyces* (eds. Strathern, Jones, and Broach) Cold Spring Harbor Lab., Cold Spring Harbor, N.Y., pp. 181–209).

Expression cassettes are typically introduced into a vector which facilitates entry into a host cell, and maintenance of the expression cassette in the host cell. Vectors that include a polynucleotide that encodes a PDI polypeptide are provided by the invention. Such vectors often include an expression cassette that can drive expression of the PDI polypeptide. To easily obtain a vector of the invention, one can clone a polynucleotide that encodes the PDI polypeptide into a commercially or commonly available vector. A variety of common vectors suitable for this purpose are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. A multicopy plasmid with selective markers such as Leu-2, URA-3, Trp-1, and His-3 is also commonly used. A number of yeast expression plasmids such as YEp6, YEp13, YEp4 can be used as expression vectors. The above-mentioned plasmids have been fully described in the literature (Botstein et al. (1979) *Gene* 8:17–24; Broach et al. (1979) *Gene,* 8:121–133). For a discussion of yeast expression plasmids, see, e.g., Parents, B., *YEAST* (1985), and Ausubel, Sambrook, and Berger, all supra). Expression in mammalian cells can be achieved using a variety of commonly available plasmids, including pSV2, pBC12BI, and p91023, as well as lytic virus vectors (e.g., vaccinia virus, adenovirus, and baculovirus), episomal virus vectors (e.g., bovine papillomavirus), and retroviral vectors (e.g., murine retroviruses).

The nucleic acids that encode the polypeptides of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes, among others. Techniques for transforming fungi are well known in the literature and have been described, for instance, by Beggs et al. ((1978) *Proc. Natl. Acad. Sci. USA* 75: 1929–1933), Yelton et al. ((1984) *Proc. Natl. Acad. Sci. USA* 81: 1740–1747), and Russell ((1983) *Nature* 301: 167–169). Procedures for transforming yeast are also well known (see, e.g., Beggs (1978) *Nature* (London), 275:104–109; and Hinnen et al. (1978) *Proc. Natl. Acad. Sci. USA,* 75:1929–1933. Transformation and infection methods for mammalian and other cells are described in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1–3, Cold Spring Harbor Laboratory, Cold Spring Harbor Press, NY, (Sambrook et al.); *Current Protocols in Molecular Biology,* F. M. Ausubel et al., eds., Current Protocols, a joint venture between Greene Publishing Associates, Inc. and John Wiley & Sons, Inc., (1994 Supplement) (Ausubel).

Once expressed, the PDI proteins can be purified, either partially or substantially to homogeneity, according to standard procedures of the art, such as, for example, ammonium sulfate precipitation, affinity columns, column chromatography, gel electrophoresis and the like (see, generally, R. Scopes, *Protein Purification,* Springer-Verlag, N.Y. (1982), Deutscher, *Methods in Enzymology Vol.* 182*: Guide to Protein Purification.,* Academic Press, Inc. N.Y. (1990)). Once purified, partially or to homogeneity as desired, the polypeptides may then be used (e.g., in screening assays for modulators for gene expression or as immunogens for antibody production).

One of skill in the art would recognize that after chemical synthesis, biological expression, or purification, the PDI protein(s) may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.,* 268: 14065–14070; Kreitman and Pastan (1993) *Bioconjug. Chem.,* 4: 581–585; and Buchner, et al., (1992) *Anal. Biochem.,* 205: 263–270). Debinski et al., for example, describe the denaturation and reduction of inclusion body proteins in guanidine-DTE. The protein is then refolded in a redox buffer containing oxidized glutathione and L-arginine.

One of skill also would recognize that modifications can be made to the PDI polypeptides without diminishing their biological activity. Some modifications may be made to facilitate the cloning, expression, or incorporation of the polypeptide into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

2. Antibodies that Specifically Bind *C. parvum* Protein Disulfide Isomerase

The invention also provides antibodies that can specifically bind *C. parvum* PDI polypeptides of the invention. These antibodies can be prepared using as immunogens natural, recombinant or synthetic polypeptides of 10 amino acids in length, or greater, selected from amino acid subsequences of the amino acid sequences shown in SEQ ID NO: 2 and SEQ ID NO: 3. Such polypeptides can function as immunogens (antigens) that can be used for the production of monoclonal or polyclonal antibodies. In one class of preferred embodiments, an immunogenic peptide conjugate is also included as an immunogen. Naturally occurring polypeptides are also used either in pure or impure form. Production of antibodies against PDI polypeptides of the invention is discussed in more detail below. In some embodiments, the antibodies of the invention can bind to polypeptides that include the amino acid sequence as shown in SEQ ID NO: 3, but do not bind substantially to PDI polypeptides that lack this amino acid sequence.

3. Nucleic Acids encoding *C. parvum* Protein Disulfide Isomerase

The invention also provides isolated and/or recombinant nucleic acids that encode the PDI polypeptides of the invention, and functional domains thereof. The nucleic acids are useful for many purposes. For example, one can use the PDI nucleic acids of the invention to produce PDI polypeptides. The nucleic acids of the invention are also useful as probes to identify PDI-encoding nucleic acids in human tissues and samples, and also in those of other mammals that can become infected by *Cryptosporidium*. The nucleic acids are also useful to study the expression of PDI, both in vitro and in vivo.

In one embodiment, the invention provides isolated nucleic acids that include a polynucleotide sequence that encodes a polypeptide that has an amino acid sequence of which at least ten consecutive amino acids are at least substantially identical to a subsequence of an amino acid sequence as set forth in SEQ ID NO: 3. Included in the invention are nucleic acids that encode a full-length PDI polypeptide that has an amino acid sequence that is substantially identical to the amino acid sequence set forth in SEQ ID NO: 2. In one presently preferred embodiment, the nucleic acids have the polynucleotide sequence as set forth in SEQ ID NO: 1.

The PDI nucleic acids of the invention can be isolated, for example, by routine cloning methods. The cDNA sequence provided in SEQ ID NO: 1 can be used to provide probes that specifically hybridize to a PDI gene, to a PDI mRNA, or to a PDI cDNA in a cDNA library (e.g., in a Southern or Northern blot). Once the target PDI nucleic acid is identified, it can be isolated according to standard methods known to those of skill in the art (see, e.g., Sambrook, Berger, and Ausubel, supra.). In another preferred embodiment, the PDI nucleic acids of the invention can be isolated by amplification methods such as polymerase chain reaction (PCR), the ligase chain reaction (LCR), the transcription-based amplification system (TAS), the self-sustained sequence replication system (SSR). A wide variety of cloning and in vitro amplification methodologies are well-known to persons of skill. Examples of these techniques and instructions sufficient to direct persons of skill through many cloning exercises are found in Berger, Sambrook, and Ausubel (all supra.); Cashion et al., U.S. Pat. No. 5,017,478; and Carr, European Patent No. 0,246,864. Examples of techniques sufficient to direct persons of skill through in vitro amplification methods are found in Berger, Sambrook, and Ausubel, as well as Mullis et al. (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) C&EN 36–47; *The Journal Of NIH Research* (1991) 3: 81–94; (Kwoh et al. (1989) *Proc. Nat'l. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077–1080; Van Brunt (1990) *Biotechnology* 8: 291–294; Wu and Wallace (1989) *Gene*, 4: 560; and Barringer et al. (1990) *Gene* 89: 117.

The invention also provides nucleic acid constructs in which a PDI polynucleotide of the invention is operably linked to a promoter that is functional in a desired host cell. Such constructs are often provided as an "expression cassette", which can also include other sequences involved in transcription, translation, and post-translational modification of the PDI polypeptide. Examples of suitable promoters and other control sequences are described herein. The invention also provides expression vectors, and host cells that comprise the PDI nucleic acids of the invention.

In presently preferred embodiments, the PDI-encoding nucleic acids of the invention have a translation initiation codon (generally ATG, or AUG in the mRNA) that is in frame with codons that encode the amino acid sequence set forth in SEQ ID NO: 3. Thus, a PDI polypeptide expressed using a PDI nucleic acid of the invention will preferably include the amino acid sequence of SEQ ID NO: 3.

B. Assay Reagents

The assays of the invention involve detecting the presence in a biological sample of a *Cryptosporidium parvum* protein disulfide isomerase (PDI), which is an antigen that is specific for *Cryptosporidium*. The invention provides assay reagents that are capable of specifically binding to the PDI antigen. These assay reagents can be used in one or more steps of the assay. For example, the assay reagents can be immobilized on a solid support and used to immobilize PDI on a solid support. Assay reagents can also be used to detect the *Cryptosporidium* antigens by, for example, attaching a detectable label to a binding moiety that binds to PDI. These are discussed in greater detail below.

The assay means for detecting PDI are, in some embodiments, binding assays. In these assays, which include immunoassays, PDI is detected using detection reagents that are capable of specifically binding to PDI. The detection reagents include at least a binding moiety and a detectable label. Suitable binding moieties include any molecule that is capable of specifically binding to PDI. Antibodies and fragments thereof are examples of binding components that are suitable for use in detection moieties.

Various procedures known in the art can be used for the production of antibodies that specifically bind to PDI. For the production of polyclonal antibodies, one can use PDI to inoculate any of various host animals, including but not limited to rabbits, mice, rats, sheep, goats, and the like. The PDI polypeptide can be prepared by recombinant means as described above using an expression vector containing a gene encoding the polypeptide; the complete nucleotide sequence is presented in SEQ ID NO: 1.

Monoclonal antibodies can be prepared by any technique that provides for the production of antibody molecules by continuous cell lines in culture, including the hybridoma technique originally developed by Kohler and Milstein ((1975) *Nature* 256: 495–497), as well as the trioma technique, the human B-cell hybridoma technique (Kozbor et al. (1983) *Immunology Today* 4: 72), and the EBV-hybridoma technique to produce human monoclonal antibodies (Cole et al. (1985) in *Monoclonal Antibodies and Cancer Therapy*, Alan R. Liss, Inc., pp. 77–96). Monoclonal antibodies also can be produced in germ-free animals as was described in PCT/US89/02545 (Publication No. WO8912690, published Dec. 12, 1989) and U.S. Pat. No. 5,091,512.

Fragments of antibodies are also useful as binding moieties. While various antibody fragments can be obtained by the digestion of an intact antibody, one of skill will appreciate that such fragments may be synthesized de novo either chemically or by utilizing recombinant DNA methodology. Thus, the term "antibody," as used herein, also includes antibody fragments either produced by the modification of whole antibodies or those synthesized de novo using recombinant DNA methodologies (e.g., single chain Fv). Single chain antibodies are also useful to construct detection moieties. Methods for producing single chain antibodies were described in, for example, U.S. Pat. No. 4,946,778. Techniques for the construction of Fab expression libraries were described by Huse et al. (1989) *Science* 246: 1275–1281; these techniques facilitate rapid identification of monoclonal Fab fragments with the desired specificity for PDI. Suitable binding moieties also include those that are obtained using methods such as phage display.

To prepare a suitable antigen preparation, one can prepare a cDNA expression library from *C. parvum* and screen the library with a polyclonal antibody that is raised against a crude preparation of PDI. The cDNA inserts from those expression plasmids that express the PDI are then subcloned and sequenced. The PDI-encoding inserts are cloned into an expression vector and used to transform *E. coli* or other suitable host cells. The resulting preparation of recombinant PDI is then used to inoculate an animal, e.g., a mouse.

In preferred embodiments, the assay reagents use recombinantly produced polyclonal or monoclonal antibodies that bind to the PDI as binding moieties. Recombinant antibodies are typically produced by immunizing an animal with the PDI, obtaining RNA from the spleen or other antibody-expressing tissue of the animal, making cDNA, amplifying the variable domains of the heavy and light immunoglobulin chains, cloning the amplified DNA into a phage display vector, infecting *E. coli*, expressing the phage display library, and selecting those library members that express an antibody that binds to PDI. Methods suitable for carrying out each of these steps are described in, for example U.S. Pat. No. 6,555,310, issued Apr. 29, 2003. In preferred embodiments, the antibody or other binding peptides are expressed on the cell surface of a replicable genetic unit, such as a filamentous phage, and especially phage M13, Fd and F1. Most work has inserted libraries encoding polypeptides to be displayed into either gIII or gVIII of these phage, forming a fusion protein which is displayed an the surface of the phage. See, e.g., Dower, WO 91119818; Devlin, WO 91/18989; MacCafferty, WO 92/01047 (gene III); Huse, WO 92/06204; Kang, WO 92/18619 (gene VIII).

In a preferred embodiment, the genes that encode the heavy and light chains of antibodies present in the cDNA library are amplified using a set of primers that can amplify substantially all of the different heavy and light chains. The resulting amplified fragments that result from the amplification step are pooled and subjected to asymmetric PCR so that only one strand (e.g., the antisense strand) is amplified. The single strand products are phosphorylated, annealed to a single-stranded uracil template (e.g., the vector BS45, described in U.S. Pat. No. 6,555,310, issued Apr. 29, 2003, which has coding regions for the constant regions of mouse heavy and light chains), and introduced into a uracil DNA glycosylase$^{+}$ host cell to enrich for vectors that contain the coding sequences for heavy and light chain variable domains.

To screen for phage that express an antibody that binds to PDI, one can attach a label to PDI using methods known to those of skill in the art. In a preferred embodiment, the phage that display such antibodies are selected using PDI to which is attached an immobilizable tag, e.g., biotin. The phage are contacted with the biotinylated antigen, after which the phage are selected by contacting the resulting complex with avidin attached to a magnetic latex bead or other solid support. The selected phage are then plated, and may be screened with PDI to which is attached a detectable label.

In a preferred embodiment, the library is enriched for those phage that display more than one antibody that binds to PDI. Methods and vectors that are useful for this enrichment are described in U.S. Pat. No. 6,555,310, issued Apr. 29, 2003. The panning can be repeated one or more times to enhance the specificity and sensitivity of the resulting antibodies. Preferably, panning is continued until the percentage of functional positives is at least about 70%, more preferably at least about 80%, and mast preferably at least about 90%.

A recombinant anti-PDI monoclonal antibody can then be selected by amplifying antibody-encoding DNA from individual plaques, cloning the amplified DNA into an expression vector, and expressing the antibody in a suitable host cell (e.g. *E. coli*). The antibodies are then tested for ability to bind PDI. An example of a recombinant monoclonal antibody prepared using this method is the mAb CP.2.

Recombinant polyclonal antibodies are particularly preferred, in particular because of the various forms of PDI that may be found in clinical samples due to, for example, proteolysis. The diverse fine binding specificity of members of a population of polyclonal antibodies often allows the population to bind to several forms of PDI (e.g., species variants, escape mutant forms, proteolytic fragments) to which a monoclonal reagent may be unable to bind. Methods for producing recombinant polyclonal antibodies are described in commonly assigned U.S. Pat. No. 6,555,310, issued Apr. 29, 2003. Specific methods of producing recombinant polyclonal antibodies that bind to PDI are described in the Examples below.

Polyclonal antibodies can be prepared as described above, except that an individual antibody is not selected. Rather, the pool of phage are used for the screening, preferably using an equal number of phage from each sample. In preferred embodiments, the phage are enriched for those that display more than one copy of the respective antibodies. The phage are then selected for those that bind to PDI. For example, one can use a biotinylated anti-PDI monoclonal antibody and PDI to concentrate those phage that express antibodies that bind to PDI. The biotinylated monoclonal antibody is immobilized on a solid support (e.g., magnetic latex) to which is attached avidin. The phage that are bound to the immobilized PDI are eluted, plated, and the panning repeated until the desired percentage of functional positives is obtained.

C. Assay Formats

The assays for detecting *Cryptosporidium* infection can be performed in any of several formats. For example, a sandwich assay can be performed by preparing a biological sample as discussed above, or as is otherwise appropriate for the particular sample, and placing the sample in contact with a solid support on which is immobilized a plurality of capture reagents that bind PDI. The PDI, if present in the sample, binds to the capture reagents. The solid support is then contacted with detection reagents for PDI. The solid support can be washed prior to contact with detection reagents to remove unbound reagents. After incubation of the detection reagents for a sufficient time to bind a substantial portion of the immobilized PDI, any unbound labeled reagents are removed by, for example, washing. The detectable label associated with the detection reagents is then detected. For example, in the case of an enzyme used as a detectable label, a substrate for the enzyme that turns a visible color upon action of the enzyme is placed in contact with the bound detection reagent. A visible color will then be observed in proportion to the amount of the specific antigen in the sample.

The capture reagent can be any compound that specifically binds to PDI. Examples of binding moieties tat are suitable for use as capture reagents are described above. One example of a suitable capture reagent is the recombinant polyclonal antibody preparation SCPc.4.PC, which was prepared as described in the Examples.

To immobilize PDI on the solid support, a capture reagent that specifically binds to PDI is non-diffusively associated with the support. The capture reagents can be non-diffusively immobilized on the support either by covalent or non-covalent methods, which are known to those of skill in the art. See, e.g., Pluskal et al. (1986) *BioTechniques* 4: 272–283. Suitable supports include, for example, glasses, plastics, polymers, metals, metalloids, ceramics, organics, and the like. Specific examples include, but are not limited to, microtiter plates, nitrocellulose membranes, nylon membranes, and derivatized nylon membranes, and also particles, such as agarose, SEPHADEX™, and the like. Assay systems for use in the methods and kits of the invention include, but are not limited to, dipstick-type devices, immunochromatographic test strips and radial partition immunoassay devices, and flow-through devices. Conveniently, where the solid support is a membrane, the sample will flow through the membrane, for example, by gravity, capillary action, or under positive or negative pressure.

Preferred assay systems for use in the kits and methods of the invention are described in EP 447154. These systems employ an apparatus that includes a porous member such as a membrane or a filter onto which is bound a multiplicity of anchor moieties for PDI. The apparatus also includes a non-absorbent member with a textured surface in communication with the lower surface of the porous member. The textured surface of the non-absorbent member can be a grooved surface such as the surface of a record or it can be composed of channels, such that when the porous and non-absorbent members are brought into contact with one another a network of capillary channels is formed. The capillary network is formed from the contact of the porous member with the textured surface of the non-absorbent member and can be constructed either before or subsequent to the initial contacting of the porous member with a fluid. In some embodiments, the capillary communication between the porous member and the non-absorbent member favors delaying the transferal of fluid from the porous member to the capillary network formed by the porous member and the textured surface of the non-absorbent member until the volume of the added fluid substantially exceeds the void volume of the porous member. The transferal of fluid from the porous member to the network of capillary channels formed by the porous member and the textured surface of the non-absorbent member can occur without the use of external means, such as positive external pressure or vacuum, or contact with an absorbent material. The devices of the present invention can also include an optional member which is placed in contact with the upper surface of the porous member and may be used to partition the upper surface of the device into discrete openings. Such openings can access either the porous member or the textured surface of the non-absorbent second member. The optional member can in conjunction with the non-absorbent member compose a fluid receiving zone in which there is no intervening porous member. A fluid receiving zone constructed from the nonabsorbent member and the optional member provides fluid capacity in addition to that provided by the network of capillary channels created by the contact of the porous member and the non-absorbent member. The openings in the optional member may include a first fluid opening and also an additional fluid opening. The first fluid opening functions as a portal for the introduction of the first fluid added to the device. The additional fluid opening serves as an additional portal through which additional fluids may be added to the inventive device.

To perform an assay using these devices, a volume of the sample is added to the porous member, where the sample permeates the void volume of the porous member and thereby contacts the anchor moieties immobilized on the porous member. In a non-competitive assay, the sample to be assayed is applied to the porous member and the PDI, if present, is bound by the anchor moieties. A detection reagent for PDI is then added as an additional fluid; these bind to the complex of PDI and capture reagent. Alternatively, the detection reagent can be added to the sample prior to application of the sample to the porous member so that the binding of detection reagent to PDI occurs prior to the binding of PDI to the capture reagent. In another embodiment, the capture reagent and detection reagent are added to the sample, after which the complex of capture reagent, PDI, and detection reagent binds to a binding agent that is either combined with these reagents or is immobilized on the porous member. An additional fluid containing reagents to effect a separation of free from bound labeled reagents can be added to remove excess detection reagent, if needed.

This device is designed to provide sufficient sensitivity to measure low concentrations of PDI because one can use large amounts of sample and efficiently remove the excess of detection reagent. Indeed, the efficient separation of free from bound label achieved by the network of capillary channels of this device improves the discrimination of specific PDI-associated signal over non-specific background signal. If needed, a signal developer solution is then added to enable the label of the detection moiety to develop a detectable signal. The signal developed can then be related to the concentration of the target ligand within the sample. In a preferred embodiment, the transfer of fluid between the porous first member of the device and the network of capillary channels formed by the contact of the porous member and textured surface of the non-absorbent second member of the device is generally self-initiated at the point when the total volume of fluid added to the device exceeds the void volume of the porous member, thus obviating the need for active interaction by the user to remove excess fluid from the analyte detection zone. The point at which the fluid transfer is initiated is dependent upon the objectives of the assay. Normally, it is desirable to contact the sample with all of the zones on the porous member which contain immobilized receptor. This method enables the detection of PDI in a manner that is simple, rapid, convenient, sensitive and efficient in the use of reagents.

Competitive binding assays can also be used to detect PDI. Conveniently, these assays are performed using the described devices by adding to a sample a labeled analog of PDI. The labeled analog and PDI present in the sample compete for the binding sites of the capture reagents. Alternatively, the capture reagents can be combined with the sample and labeled analogs with subsequent immobilization of the capture reagents onto the porous member through contact with a binding agent. An additional fluid to separate the free from bound label may be added to the device, followed if needed by a signal development solution to enable detection of the label of the labeled analog which has complexed with capture reagent immobilized on the porous member. The amount of labeled PDI bound to the porous member is related to the concentration of PDI in the sample.

This invention also provides kits for the detection and/or quantification of PDI by the described methods. The kits can include a container containing one or more of the above-discussed detection reagents with or without labels, and capture reagents, either free or bound to solid supports. Also included in the kits can be a suitable membrane, preferably in the form of an assay apparatus that is adapted to use in the described assay. Preferably, the kits will also include reagents used in the described assays, including reagents useful for detecting the presence of the detectable labels. Other materials useful in the performance of the assays can also be included in the kits, including test tubes, transfer pipettes, and the like. The kits can also include written instructions for the use of one or more of these reagents in any of the assays described herein.

The kits of the invention can also include an internal and/or an external control. An internal control can consist of the PDI polypeptide. The control antigen can conveniently be preattached to a capture reagent in a zone of the solid support adjacent to the zone to which the sample is applied. The external control can also consist of the PDI polypeptide. Typically, the antigen present in the external control will be at a concentration at or above the sensitivity limit of the assay means. The external control antigen can be diluted in the sample diluent and assayed in the same manner as would a biological sample. Alternatively, the external control PDI polypeptide can be added to an aliquot of an actual biological sample to determine the sensitivity of the assay. The kits of the present invention can contain materials sufficient for one assay, or can contain sufficient materials for multiple assays.

The methods, compositions and kits provided by the invention are capable of detecting PDI with high sensitivity. The assays and kits will detect PDI when present in a sample at a concentration of about 100 ng/ml or less. Preferably, the detection limit for PDI will be about 20 ng/ml or less, more preferably about 4 ng/ml or less, and still more preferably the detection limit for PDI will be about 1 ng/ml or less.

D. Detection Reagents

The presence of PDI is generally detected using a detection reagent that is composed of a binding moiety that specifically binds to PDI. The detection reagents are either directly labeled, i.e., comprise or react to produce a detectable label, or are indirectly labeled, i.e., bind to a molecule comprising or reacting to produce a detectable label. Labels can be directly attached to or incorporated into the detection reagent by chemical or recombinant methods.

In one embodiment, a label is coupled to a molecule, such as an antibody that specifically binds to PDI, through a chemical linker. Linker domains are typically polypeptide sequences, such as poly gly sequences of between about 5 and 200 amino acids. In some embodiments, proline residues are incorporated into the linker to prevent the formation of significant secondary structural elements by the linker. Preferred linkers are often flexible amino acid subsequences which are synthesized as part of a recombinant fusion protein comprising the RNA recognition domain. In one embodiment, the flexible linker is an amino acid subsequence that includes a proline, such as Gly(x)-Pro-Gly(x) where x is a number between about 3 and about 100. In other embodiments, a chemical linker is used to connect synthetically or recombinantly produced recognition and labeling domain subsequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

The detectable labels used in the assays of the present invention, which are attached to the detection reagent, can be primary labels (where the label comprises an element that is detected directly or that produces a directly detectable element) or secondary labels (where the detected label binds to a primary label, e.g., as is common in immunological labeling). An introduction to labels, labeling procedures and detection of labels is found in Polak and Van Noorden (1997) *Introduction to Immunocytochemistry*, 2nd ed., Springer Verlag, NY and in Haugland (1996) *Handbook of Fluorescent Probes and Research Chemicals*, a combined handbook and catalogue Published by Molecular Probes, Inc., Eugene, Oreg. Patents that described the use of such labels include U.S. Pat. Nos. 3,817,837; 3,850,752; 3,939,350; 3,996,345; 4,277,437; 4,275,149; and 4,366,241.

Primary and secondary labels can include undetected elements as well as detected elements. Useful primary and secondary labels in the present invention can include spectral labels such as green fluorescent protein, fluorescent dyes (e.g., fluorescein and derivatives such as fluorescein isothiocyanate (FITC) and Oregon Green™, rhodamine and derivatives (e.g., Texas red, tetrarhodimine isothiocynate (TRITC), etc.), digoxigenin, biotin, phycoerythrin, AMCA, CyDyes™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectral colorimetric labels such as colloidal gold or colored glass or plastic (e.g. polystyrene, polypropylene, latex, etc.) beads. The label can be coupled directly or indirectly to a component of the detection assay (e.g., the detection reagent) according to methods well known in the art. As indicated above, a wide variety of labels may be used, with the choice of label depending on sensitivity required, ease of conjugation with the compound, stability requirements, available instrumentation, and disposal provisions.

Preferred labels include those that use: 1) chemiluminescence (using horseradish peroxidase and/or alkaline phosphatase with substrates that produce photons as breakdown products as described above) with kits being available, e.g., from Molecular Probes, Amersham, Boehringer-Mannheim, and Life Technologies/Gibco BRL; 2) color production (using both horseradish peroxidase and/or alkaline phosphatase with substrates that produce a colored precipitate (kits available from Life Technologies/Gibco BRL, and Boehringer-Mannheim)); 3) fluorescence using, e.g., an enzyme such as alkaline phosphatase, together with the substrate AttoPhos (Amersham) or other substrates that produce fluorescent products, 4) fluorescence (e.g., using Cy-5 (Amersham), fluorescein, and other fluorescent tags); 5) radioactivity. Other methods for labeling and detection will be readily apparent to one skilled in the art.

For use of the present invention in the clinic, preferred labels are non-radioactive and readily detected without the necessity of sophisticated instrumentation. Preferably, detection of the labels will yield a visible signal that is immediately discernable upon visual inspection. One preferred example of detectable secondary labeling strategies uses an antibody that recognizes PDI in which the antibody is linked to an enzyme (typically by recombinant or covalent chemical bonding). The antibody is detected when the enzyme reacts with its substrate, producing a detectable product. Preferred enzymes that can be conjugated to detection reagents of the invention include, e.g., β-galactosidase, luciferase, horse radish peroxidase, and alkaline phosphatase. The chemiluminescent substrate for luciferase is luciferin. One embodiment of a fluorescent substrate for β-galactosidase is 4-methylumbelliferyl-β-D-galactoside. Embodiments of alkaline phosphatase substrates include p-nitrophenyl phosphate (pNPP), which is detected with a spectrophotometer; 5-bromo-4-chloro-3-indolyl phosphate/ nitro blue tetrazolium (BCIP/NBT) and fast red/napthol AS-TR phosphate, which are detected visually; and 4-methoxy-4-(3-phosphonophenyl) spiro[1,2-dioxetane-3,2'-adamantane], which is detected with a luminometer. Embodiments of horse radish peroxidase substrates include 2,2'azino-bis(3-ethylbenzthiazoline-6 sulfonic acid)

(ABTS), 5-aminosalicylic acid (5AS), o-dianisidine, and o-phenylenediamine (OPD), which are detected with a spectrophotometer; and 3,3,5,5'-tetramethylbenzidine (TMB), 3,3'diaminobenzidine (DAB), 3-amino-9-ethylcarbazole (AEC), and 4-chloro-1-naphthol (4C1N), which are detected visually. Other suitable substrates are known to those skilled in the art. The enzyme-substrate reaction and product detection are performed according to standard procedures known to those skilled in the art and kits for performing enzyme immunoassays are available as described above.

The presence of a label can be detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeling moieties is digitized for subsequent computer analysis.

EXAMPLES

The following examples are offered to illustrate, but not to limit the present invention.

Example 1

Synthesis and Screening of a *Cryptosporidium parvum* Mixed cDNA Library

This Example describes the cloning of cDNAs that encode the protein disulfide isomerase antigen of *C. parvum*.

A. Culture of *C. Parvum* and Preparation of Soluble Antigen

*Cryptosporidium parvum* oocysts were obtained from the Tufts University School of Veterinary Medicine. Organisms were harvested and washed three times in 0.01M phosphate buffered saline (PBS), pH 7.6. The cell pellet was resuspended in 1 ml of PBS and subjected to 4 cycles of flash-freezing and thawing. *Cryptosporidium* oocysts were sonicated for 12 min using a VirSonic 475 Ultrasonic Cell Disrupter. Cell disruption was monitored by microscopic inspection. Cells and debris were removed by centrifugation at 14,000×g for 20 min at 4° C. The supernatant containing soluble antigen was transferred to a fresh tube, assayed for protein content, and used for immunizations.

Freshly harvested *C. parvum* oocysts from bovine feces (originally of human origin) were obtained from Utah State University, Logan, Utah and Turts University, Boston, Mass. Excystation of sporozoites was performed by the method of Yang et al. (1996) *Infect. Immun.* 64: 349–354. Sporozoites were cultured in MDCK cells grown in a 5% $CO_2$ environment at 37° C. Organisms were harvested from MDCK cell culture supernatants by an initial centrifugation for 10 min at 500×g to remove detached cells and large cellular debris, followed by centrifugation for 20 min at 10,000×g. The pellet was washed three times in sterile PBS.

The entire life cycle of *C. parvum* was reproduced by infecting a monolayer of bovine fallopian tube epithelial cells (BFTE) in 25 $cm^2$ tissue culture flasks with approximately $10^4$ sporozoites and incubating 24–72 hr at 37° C. in a candle jar environment (Yang et al., supra.). The organisms from the BFTE cell culture supernatant were purified by passage through a 3 mm pore size polycarbonate filter (Millipore Corp, Bedford, Mass.). This filtration step permitted the passage of oocysts and sporozoites while retaining cellular debris. Organisms were concentrated by an initial centrifugation for 20 min at 10,000×g. The pellet was then washed three times in sterile PBS. The pellet containing organisms representing all forms of the *C. parvum* life cycle was pooled with the sporozoite pellet purified from the MDCK cell culture above and used immediately for the isolation of total RNA.

B. Isolation and Purification of RNA from a *Cryptosporidium parvum* Mixed Culture

*Cryptosporidium parvum* organisms representing all phases of its life cycle (oocysts and sporozoites) were cultured and harvested as described above. Working quickly, 1.0 ml of solution D (25.0 g guanidine thiocyanate (Boehringer Mannheim, Indianapolis, Ind.), 29.3 ml sterile water, 1.76 ml 0.75M sodium citrate (pH 7.0), 2.64 ml 10% sarkosyl (Fisher Scientific, Pittsburgh, Pa.), 0.36 ml 2-mercaptoethanol (Fisher Scientific, Pittsburgh, Pa.)) was added to the pellet while vortexing. The cell suspension was pulled through an 18-gauge needle until viscous and all cells were lysed, after which the suspension was transferred to a microcentrifuge tube. The suspension was then pulled through a 22-gauge needle followed by a 25-gauge needle an additional 5–10 times.

The sample was divided evenly between two microcentrifuge tubes and the following added in order, with mixing by inversion after each addition: 100 μl 2M sodium acetate (pH 4.0), 1.0 ml water saturated phenol (Fisher Scientific, Pittsburgh, Pa.): 200 μl chloroform/isoamyl alcohol 49:1 (Fisher Scientific, Pittsburgh, Pa.). The solution was vortexed for 10 seconds and incubated on ice for 15 minutes. Following centrifugation (10,000 g) for 20 minutes at 2–8° C., the aqueous phase was transferred to a fresh tube. An equal volume of water saturated phenol:chloroform:isoamyl alcohol (50:49:1) was added, and the tube was vortexed for ten seconds. After a 15 min incubation on ice, the sample was centrifuged for 20 minutes at 2–8° C., and the aqueous phase was transferred to a fresh tube and precipitated with an equal volume of isopropanol at −20° C. for a minimum of 30 minutes. Following centrifugation (10,000 g) for 20 minutes at 4° C., the supernatant was aspirated away, the tubes briefly spun and all traces of liquid removed.

The RNA pellets were each dissolved in 300 μl of solution D, combined, and precipitated with an equal volume of isopropanol at −20° C. for a minimum of 30 minutes. The sample was centrifuged (10,000 g) for 20 minutes at 4° C., the supernatant aspirated as before, and the sample rinsed with 100 μl of ice-cold 70% ethanol. The sample was again centrifuged (10,000 g) for 20 minutes at 4° C., the 70% ethanol solution aspirated, and the RNA pellet dried in vacuo. The pellet was resuspended in 100 μl of sterile distilled water. The concentration was determined by $A_{260}$ using an absorbance of 1.0 for a concentration of 40 μg/ml. The RNAs were stored at −80° C.

Messenger RNA (mRNA) was purified from total RNA using an Oligotex Mini-Kit™ mRNA isolation kit (Qiagen, Santa Clarita, Calif.) according to the manufacturer's recommendations. The concentration of mRNA was determined by $A_{260}$ using an absorbance of 1.0 for a concentration of 40 μg/ml. The mRNAs were stored at −80° C.

C. Synthesis of Lambda cDNA Libraries.

The mRNAs (5.0 μg) purified above were used to synthesize the first and second strands of cDNA using a cDNA synthesis kit (Stratagene, San Diego, Calif.) following the manufacturer's recommendations. The resulting cDNA was selected for inserts greater than 500 base pairs in length. The size-selected cDNA was then ligated into the Uni-ZAP XR vector (Stratagene, San Diego, Calif.) and packaged with Gigapak Gold packaging extract (Stratagene, San Diego, Calif.) following manufacturer's recommendations. The primary sizes for the mixed library were determined by plating serial dilutions of the packaged library (see below) to be 1.4×10⁶ plaque-forming units (pfu). Background was determined to be <2.0% through blue/white selection (see below). The resulting Uni-ZAP XR™ lambda phage library was amplified once before screening to ensure stability of the library, titered, and stored at 4° C.

D. Plating Lambda Phage cDNA Library.

Starting with a lambda phage stock, a series of 100-fold dilutions (10 µl to 1.0 ml) were made in SM buffer (Stratagene, San Diego, Calif.). The diluted phage samples (10 µl) were added to 200 µl of an overnight culture of *Escherichia coli* strain XL1-Blue MRF' (Stratagene, San Diego, Calif.) adjusted to $OD_{600}$=0.5 in 10 mM $MgSO_4$ in sterile 15 ml tubes and incubated at 37° C. for 15 min. After adding 3.0 ml of NZY top-agar at 55° C., the mixture was poured and evenly distributed on an NZY agar plate (100 mm) that had been pre-warmed (37° C.–55° C.) to remove any excess moisture on the agar surface. The plates were cooled to room temperature, at which time the top-agar solidified, and the plates were then inverted and placed at 37° C. For titering purposes, the plates were left at 37° C. overnight and the number of plaques counted and a titer determined.

In order to determine the background for the library (the percentage of clones not carrying an insert), several hundred plaques were plated as described above. Prior to plating, 15 µl of 0.5M isopropyl-β-D-thiogalactoside (IPTG) and 50 µl of 5-bromo-4-chloro-3-indoyl-β-D-galctopyranoside (X-gal) [250 mg/ml (in dimethylformamide)] was added to the NZY top agar. These plates were incubated at 37° C. for 6–8 hours and transferred to room temperature overnight. Plaques that stained blue correspond to clones that do not have an insert, while non-staining, white plaques contain an insert. The percentage of background plaques was calculated by dividing the number of blue plaques by the total number of plaques.

E. Screening of *C. parvum* Mixed cDNA Libraries with Monoclonal Antibody CP.2

The *C. parvum* mixed cDNA library was plated, separately, on large (150 mm) NZY agar plates at a density of approximately 10,000–20,000 pfu/plate as described above, except that 600 µl of $OD_{600}$=0.5 XL1-Blue cells and nine ml of NZY top agar were used for plating. When the plaques reached 0.5–1.0 mm in diameter (4–5 hr), nitrocellulose filter lifts (diameter 137 mm, pore size 0.45 µm, BA85 Protran, Schleicher and Schuell, Keene, N.H.) soaked in 10 mM isopropyl-β-D-thiogalactoside (IPTG) were placed on the agar plates, marked asymmetrically with a needle, and placed at 20° C.

After overnight incubation, the filters were carefully removed from the plates with membrane forceps, rinsed briefly in TBST (40 mM TRIS, 150 mM NaCl, 0.05% Tween 20 (Fisher Chemical, Pittsburgh, Pa.), pH 7.5) to remove any debris from the lifts, and incubated for greater than one hour in block (1% BSA solution containing 20 mM Tris, 150 mM NaCl, and 0.1% sodium azide, pH 8.0). The filters were then incubated in CP.2-alkaline phosphatase (AP) conjugate (Example 19A) at 2.5 µg/ml, in block, for a minimum of 4 hours. The filters were washed three times with TBST for 5 min each. After the final wash, the filters were developed as described in Example 13.

The filters were aligned with the agar plates through the asymmetric needle marks and plaques individually cored from the agar plates and transferred to 250–500 µl of SM buffer. The plaques were chosen based on their staining intensity with CP.2-AP conjugate, ranging from light staining to dark staining. These plaques were purified to homogeneity through iterative rounds of the plating/filter lift procedure described above.

The DNA inserts were subcloned 'rescued' into the plasmid vector pBluescript (Stratagene, San Diego, Calif.) through an in vivo excision process following the manufacturer's recommendations. The DNA sequence at the 3' end of each clone was determined by the dideoxy chain termination method using Sequenase II™ DNA cloning kit (U.S. Biochemical) and an oligonucleotide, primer A (Table 1), that binds to the DNA sequence on the 3' side of the insert in the pBluescript vector. One clone was sequenced. The polynucleotide sequence of the cDNA (SEQ ID NO: 1) and the deduced amino acid sequence (SEQ ID NO: 2) are presented in FIG. 3A and FIG. 3B, respectively.

Example 2

Cloning of the *Cryptosporidium parvum* Protein Disulfide Isomerase cDNA

PCR primers were made corresponding to the coding sequence at the 5' and 3' ends of the *C. parvum* PDI, primers B and C, respectively (Table 1). The primers were based on a sequence found in the literature (Blunt et al., supra.). In addition, the 5' primer contains 20 base pairs of vector sequence at its 5'-end corresponding to the 3'-end of the pBRnsiH3 vector (described in commonly assigned U.S. Pat. No. 6,555,310, issued Apr. 29, 2003. The 3' primer contains the 19 base pairs of the tet promoter removed by HindIII digestion, in addition to 20 base pairs of vector sequence 3' to the HindIII site at its 5' end (see, Example 18 of U.S. Pat. No. 6,555,310, issued Apr. 29, 2003).

The PDI insert was amplified with the primers described above and 1 µl (~50 ng) of *C. parvum* genomic DNA as template per reaction. The amplification (3×100 µl reactions) was performed using Expand™ DNA polymerase and the reactions pooled and purified as described in Example 19 of U.S. Pat. No. 6,555,310. The PDI insert (100 ng) was annealed with the pBRnsiH3 (100 ng) at a 3:1 molar excess of insert to vector, and an aliquot electroporated into 40 µl of electrocompetent *E. coli* strain, DH10B as described in Example 9. The transformed cells were diluted to 1.0 ml with 2×YT broth and 10 µl, 100 µl, and 300 µl plated on LB agar plates supplemented with tetracycline (10 µg/ml) and grown overnight at 37° C. Four colonies were picked into 3 ml 2×YT supplemented tetracycline (10 µg/ml) and grown overnight at 37° C. The following day, glycerol freezer stocks were made for long term storage at −80° C.

These four clones were sequenced by the dideoxy chain termination method using a Sequenase II™ DNA cloning kit (U.S. Biochemical) and oligonucleotide primers D–L (Table 1). Primers D–J bind to the protein disulfide isomerase DNA sequence and primers K and L (Table 1) bind on the 5' and 3' side of the insert in the pBR vector, respectively. The nucleotide sequence of the PDI cDNA (SEQ ID NO: 1), and the corresponding deduced amino acid sequence (SEQ ID NO: 2), are presented in FIG. 3A and FIG. 3B, respectively.

A search of the cDNA polynucleotide sequence against the National Center for Biotechnology Information (NCBI) non-redundant nucleotide database using the BLAST search engine revealed that the clone has a deduced amino acid sequence similar to that of *Cryptosporidium parvum* protein disulfide isomerase (PDI) (Blunt et al. (1996) *Gene* 181: 221–223). Two significant differences were found in the four clones isolated as described herein as compared to the Blunt et al. sequence. The first was a single base insertion (G) between positions 1065 and 1066 (numbering based on Genbank Accession No. U48261). The second was the deletion of a single base (C) at position 1161 (numbering based on Genbank Accession No. U48261). These changes resulted in a frame-shift spanning 32 amino acids.

A comparison of the *Cryptosporidium parvum* protein disulfide isomerase protein sequence as described herein to that of the previously reported amino acid sequence for *C.*

*parvum* PDI (Blunt et al. (1996) *Gene* 181: 221–223) revealed a 32 amino acid region in which the amino acid sequences diverge (shown below). The numbering at the beginning and ending of the sequence corresponds to the numbering convention used by Blunt et al. The 32 amino acid region that differs between the two sequences is highlighted in bold type.

Mice were immunized intraperitoneally or subcutaneously with *C. parvum* soluble antigen (Example 1A) using 50 μg protein in Freund's complete adjuvant on day 0, and with 100 μg antigen on day 28. Tests bleeds of mice were obtained through puncture of the retro-orbital sinus. If, by testing the titers, they were deemed high by ELISA using

```
Applicants    250 SREGYTAWFCGTNEDFAKYASNIRKVAADYREKYAFVFLDT 290 (SEQ ID NO: 5)

Blunt et al.  250 SREGYTPGSVVLTRTSPSMLQTLERLQLITEKSMPLFSLDT 290 (SEQ ID NO: 4)
```

The nucleotide sequence of the region of Applicants' PDI sequence that differs from that of Blunt et al. is: shown in FIG. 3A.

The inventors believe that PDI sequence described herein is the coned sequence based on the following: 1) the identical insertion and deletion occurred in four clones from two independent cloning experiments; 2) the frame-shifted sequence described herein shares a greater percent identity to protein disulfide isomerase from other organisms than does the same region from the literature. The *Cryptosporidium parvum* protein disulfide isomerase antigen was expressed and purified as described in Example 15.

biotinylated antigen immobilized via streptavidin, the mice were boosted with 100 μg of protein on day 70, 71 and 72, with subsequent sacrifice and splenectomy on day 77. If titers of antibody were not deemed satisfactory, mice were boosted with 100 μg antigen on day 56 and a test bleed taken on day 63. If satisfactory titers were obtained, the animals were boosted with 100 μg of antigen on day 98, 99, and 100 and the spleens harvested on day 105.

The spleens were harvested in a laminar flow hood and transferred to a petri dish, trimming off and discarding fat and connective tissue. The spleens were, working quickly,

TABLE 1

PCR and Sequencing Primer Sequences

```
A: 5'-GTAAAACGACGGCCAGTGAATTG-3'                              (SEQ ID NO:6)

B: 5'-ACCCGTTTTTTGGATGGAGTGAAACGATGATCGGAATTCGTAGCTTGG        (SEQ ID NO:7)
      TTTCA-3'

C: 5'-GTGATAAACTACCGCATTAAAGCTTATCGATGATAAGCTGTCAATTAG        (SEQ ID NO:8)
      TGATGGTGATGGTGATGGAGTTCGTCACGAGATTCCTTTTC-3'

D: 5'-TCCAAGGTAGTCTTGGGTGG-3'                                  (SEQ ID NO:9)

E: 5'-AAGCTCTCTCCCCCAGTACA-3'                                  (SEQ ID NO:10)

F: 5'-GCAGTCCAAGTTGCTGAATC-3'                                  (SEQ ID NO:11)

G: 5'-CTCGAGGTATTACACAAGGA-3'                                  (SEQ ID NO:12)

H: 5'-CCAAGTATGCTTCAAACATT-3'                                  (SEQ ID NO:13)

I: 5'-TTCGACTCTGTTGAGCCATT-3'                                  (SEQ ID NO:14)

J: 5'-TGTGGACACTGTAAGAACCTC-3'                                 (SEQ ID NO:15)

K: 5'-GAGGATGACGATGAGCGC-3'                                    (SEQ ID NO:16)

L: 5'-GCAACTCTCTACTGTTTCTCC-3'                                 (SEQ ID NO:17)

M: 5'-TCGCTGCCCAACCAGCCATG-3'                                  (SEQ ID NO:18)

N: 5'-GTGATAAACTACCGCATTAAAGCTTATCGATGATAAGCTGTCAATTA         (SEQ ID NO:19)
      GTGATGGTGATGGTGATGACAATCCCTG-3'
```

Example 3

Immunization of Mice with Crude *Cryptosporidium* Soluble Antigen and Purification of RNA from Mouse Spleens Mice were immunized by the following method based on experience of the timing of spleen harvest for optimal recovery of mRNA coding for antibody. Two species of mice were used: Balb/c (Charles River Laboratories, Wilmington, Mass.) and A/J (Jackson Laboratories, Bar Harbor, Me.).

macerated with the plunger from a sterile 5 cc syringe in the presence of 1.0 ml of solution D (25.0 g guanidine thiocyanate (Boehringer Mannheim, Indianapolis, Ind.), 29.3 ml sterile water, 1.76 ml 0.75 M sodium citrate (pH 7.0), 2.64 ml 10% sarkosyl (Fisher Scientific, Pittsburgh, Pa.), 0.36 ml 2-mercaptoethanol (Fisher Scientific, Pittsburgh, Pa.)). The spleen suspension was pulled through an 18 gauge needle until viscous and all cells were lysed, then transferred to a microcentrifuge tube. The petri dish was washed with 100 μl of solution D to recover any remaining spleen, and this was transferred to the tube. The suspension was then pulled through a 22 gauge needle an additional 5–10 times.

The sample was divided evenly between two microcentrifuge tubes and the following added, in order, with mixing by inversion after each addition: 100 µl 2 M sodium acetate (pH 4.0), 1.0 ml water-saturated phenol (Fisher Scientific, Pittsburgh, Pa.): 200 µl chloroform/isoamyl alcohol 49:1 (Fisher Scientific, Pittsburgh, Pa.). The solution was vortexed for 10 seconds and incubated on ice for 15 min. Following centrifugation at 14 krpm for 20 min at 2–8° C., the aqueous phase was transferred to a fresh tube. An equal volume of water saturated phenol:chloroform:isoamyl alcohol (50:49:1) was added, and the tube was vortexed for ten seconds. After a 15 min incubation on ice, the sample was centrifuged for 20 min at 2–8° C., and the aqueous phase was transferred to a fresh tube and precipitated with an equal volume of isopropanol at −20° C. for a minimum of 30 min. Following centrifugation at 14 krpm for 20 min at 4° C., the supernatant was aspirated away, the tubes briefly spun and all traces of liquid removed.

The RNA pellets were each dissolved in 300 µl of solution D, combined, and precipitated with an equal volume of isopropanol at −20° C. for a minimum of 30 min. The sample was centrifuged 14 krpm for 20 min at 4° C., the supernatant aspirated as before, and the sample rinsed with 100 µl of ice-cold 70% ethanol. The sample was again centrifuged 14 krpm for 20 min at 4° C., the 70% ethanol solution aspirated, and the RNA pellet dried in vacuo. The pellet was resuspended in 100 µl of sterile distilled water. The concentration was determined by $A_{260}$ using an absorbance of 1.0 for a concentration of 33 µg/ml. The RNAs were stored at −80° C.

Example 4

Preparation of Complementary DNA (cDNA)

The total RNA purified from mouse spleens as described above was used directly as template for cDNA preparation. RNA (50 µg) was diluted to 100 µL with sterile water, and 10 µL of 130 ng/µL oligo $dT_{12}$ (synthesized on Applied Biosystems Model 392 DNA synthesizer) was added. The sample was heated for 10 min at 70° C., then cooled on ice. Forty µL 5× first strand buffer was added (Gibco/BRL, Gaithersburg, Md.), along with 20 µL 0.1 M dithiothreitol (Gibco/BRL, Gaithersburg, Md.), 10 µL 20 mM deoxynucleoside triphosphates (dNTP's, Boehringer Mannheim, Indianapolis, Ind.), and 10 µL water on ice. The sample was then incubated at 37° C. for 2 min. Ten µL reverse transcriptase (Superscript™ II, Gibco/BRL, Gaithersburg, Md.) was added and incubation was continued at 37° C. for 1 hr. The cDNA products were used directly for polymerase chain reaction (PCR).

Example 5

Amplification of cDNA by PCR

To amplify substantially all of the H and L chain genes using PCR, primers were chosen tat corresponded to substantially all published sequences. Because the nucleotide sequences of the amino terminals of H and L contain considerable diversity, 33 oligonucleotides were synthesized to serve 5' primers for the H chains, and 29 oligonucleotides were synthesized to serve as 5' primers for the kappa L chains as described in commonly assigned U.S. Pat. No. 6,555,310, issued Apr. 29, 2003. The constant region nucleotide sequences required only one 3' primer each to the H chains and the kappa L chains. Id.

A 50 µL reaction was performed for each primer pair with 50 pmol of 5' primer, 50 pmol of 3' primer, 0.25 µL Taq DNA Polymerase (5 units/µL, Boehringer Mannheim, Indianapolis, Ind.), 3 µL cDNA (prepared as described in Example 4), 5 µL 2 mM dNTP's, 5 µL 10×Taq DNA polymerase buffer with $MgCl_2$ (Boehringer Mannheim, Indianapolis, Ind.), and $H_2O$ to 50 µL. Amplification was done using a GeneAmp® 9600 thermal cycler (Perkin Elmer, Foster City, Calif.) with the following program: 94° C. for 1 min; 30 cycles of 94° C. for 20 sec, 55° C. for 30 sec, and 72° C. for 30 sec; 72° C. for 6 min; 4° C.

The dsDNA products of the PCR process were then subjected to asymmetric PCR using only a 3' primer to generate substantially only the anti-sense strand of the target genes. A 100 µL reaction was done for each dsDNA product with 200 pmol of 3' primer, 2 µL of ds-DNA product, 0.5 µL Taq DNA Polymerase, 10 µL 2 mM dNTP's, 10 µL 10×Taq DNA polymerase buffer with $MgCl_2$ (Boehringer Mannheim, Indianapolis, Ind.), and $H_2O$ to 100 µL. The same PCR program as that described above was used to amplify the single-stranded (ss)-DNA.

Example 6

Purification of ss-DNA by High Performance Liquid Chromatography and Kinasing ss-DNA The H chain ss-PCR products and the L chain ss-PCR products were ethanol precipitated by adding 2.5 volumes ethanol and 0.2 volumes 7.5 M ammonium acetate and incubating at −20° C. for at least 30 min. The DNA was pelleted by centrifuging in an Eppendorf centrifuge at 14 krpm for 10 min at 2–8° C. The supernatant was carefully aspirated, and the tubes were briefly spun a 2nd time. The last drop of supernatant was removed with a pipette. The DNA was dried in vacuo for 10 min on medium heat. The H chain products were pooled in 210 µL water and the L chain products were pooled separately in 210 µL water. The ss-DNA was purified by high performance liquid chromatography (HPLC) using a Hewlett Packard 1090 HPLC and a Gen-Pak™ FAX anion exchange column (Millipore Corp., Milford, Mass.). The gradient used to purify the ss-DNA is shown in Table 2, and the oven temperature was at 60° C. Absorbance was monitored at 260 nm. The ss-DNA eluted from the HPLC was collected in 0.5 min fractions. Fractions containing ss-DNA were ethanol precipitated, pelleted and dried as described above. The dried DNA pellets were pooled in 200 µL sterile water.

TABLE 2

| HPLC gradient for purification of ss-DNA | | | | |
|---|---|---|---|---|
| Time (min) | % A | % B | % C | Flow (ml/min) |
| 0 | 70 | 30 | 0 | 0.75 |
| 2 | 40 | 60 | 0 | 0.75 |
| 32 | 15 | 85 | 0 | 0.75 |
| 35 | 0 | 100 | 0 | 0.75 |
| 40 | 0 | 100 | 0 | 0.75 |
| 41 | 0 | 0 | 100 | 0.75 |
| 45 | 0 | 0 | 100 | 0.75 |
| 46 | 0 | 100 | 0 | 0.75 |
| 51 | 0 | 100 | 0 | 0.75 |
| 52 | 70 | 30 | 0 | 0.75 |

Buffer A is 25 mM Tris, 1 mM EDTA, pH 8.0
Buffer B is 25 mM Tris, 1 mM EDTA, 1 M NaCl, pH 8.0
Buffer C is 40 mM phosphoric acid BufTer A is 25 mM Tris, 1 mM EDTA, pH 8.0 Buffer B is 25 mM Tris, 1 mM BDTA, 1 M NaCi, pH 8.0 Buffer C is 40 mM phosphoric acid The ss-DNA was phosphorylated on the 5' end in preparation for mutagenesis (Example 8). Twenty-four μL 10× kinase buffer (United States Biochemical, Cleveland, Ohio), 10.4 μL 10 mM adenosine-5'-triphosphate (Boehringer Mannheim, Indianapolis, Ind.), and 2 μL polynucleotide kinase (30 units/μL, United States Biochemical, Cleveland, Ohio) was added to each sample, and the tubes were incubated at 37° C. for 1 hr. The reactions were stopped by incubating the tubes at 70° C. for 10 min. The DNA was purified with one extraction of equilibrated phenol (pH>8.0, United States Biochemical, Cleveland, Ohio):chloroform:isoamyl alcohol (50:49:1) and one extraction with chloroform:isoamyl alcohol (49:1). After the extractions, the DNA was ethanol precipitated and pelleted as described above. The DNA pellets were dried, then dissolved in 50 μL sterile water. The concentration was determined by measuring the absorbance of an aliquot of the DNA at 260 nm using 33 μg/ml for an absorbance of 1.0. Samples were stored at −20° C.

Example 7

Preparation of Uracil Templates Used in Generation of Spleen Antibody Phage Libraries One ml of *E. coli* CJ236 (BioRAD, Hercules, Calif.) overnight culture was added to 50 ml 2×YT in a 250 ml baffled shake flask. The culture was grown at 37° C. to $OD_{600}$=0.6, inoculated with 10 μl of a 1/100 dilution of BS45 vector phage stock (described in commonly assigned U.S. Pat. No. 6,555,310, issued Apr. 29, 2003) and growth continued for 6 hr. Approximately 40 ml of the culture was centrifuged at 12 krpm for 15 minutes at 4° C. The supernatant (30 ml) was transferred to a fresh centrifuge tube and incubated at room temperature for 15 minutes after the addition of 15 μl of 10 ml/mt RNaseA (Boehringer Mannheim, Indianapolis, Ind.). The phage were precipitated by the addition of 7.5 ml of 20% polyethylene glycol 8000 (Fisher Scientific, Pittsburgh, Pa.)/3.5M ammonium acetate (Sigma Chemical Co., St. Louis, Mo.) and incubation on ice for 30 min. The sample was centrifuged at 12 krpm for 15 min at 2–8° C. The supernatant was carefully discarded, and the tube was briefly spun to remove all traces of supernatant. The pellet was resuspended in 400 μl of high salt buffer (300 mM NaCl, 100 mM Tris pH 8.0, 1 mM EDTA), and transferred to a 1.5 ml tube.

The phage stock was extracted repeatedly with an equal volume of equilibrated phenol:chloroform:isoamyl alcohol (50:49:1) until no trace of a white interface was visible, and then extracted with an equal volume of chloroform:isoamyl alcohol (49:1). The DNA was precipitated with 2.5 volumes of ethanol and ⅕ volume 7.5 M ammonium acetate and incubated 30 min at −20° C. The DNA was centrifuged at 14 krpm for 10 min at 4° C., the pellet washed once with cold 70% ethanol, and dried in vacuo. The uracil template DNA was dissolved in 30 μl sterile water and the concentration determined by $A_{260}$ using an absorbance of 1.0 for a concentration of 40 μg/ml. The template was diluted to 250 ng/μl with sterile water, aliquoted, and stored at −20° C.

Example 8

Mutagenesis of Uracil Template with ss-DNA and Electroporation into *E. coli* to Generate Antibody Phage Libraries Antibody phage display libraries were generated by simultaneously introducing single-stranded heavy and light chain genes onto a phage display vector uracil template. A typical mutagenesis was performed on a 2 μg scale by mixing the following in a 0.2 ml PCR reaction tube: 8 μl of (250 ng/μl) uracil template (Example 7), 8 μl of 10× annealing buffer (200 mM Tris pH 7.0, 20 mM $MgCl_2$, 500 mM NaCl), 3.33 μl of kinased single-stranded heavy chain insert (100 ng/μl), 3.1 μl of kinased single-stranded light chain insert (100 ng/μl), and sterile water to 80 μl. DNA was annealed in a GeneAmp® 9600 thermal cycler using the following thermal profile: 20 sec at 94° C., 85° C. for 60 sec, 85° C. to 55° C. ramp over 30 min, hold at 55° C. for 15 min. The DNA was transferred to ice after the program finished. The extension/ligation was carried out by adding 8 μl of 10× synthesis buffer (5 mM each dNTP, 10 mM ATP, 100 mM Tris pH 7.4, 50 mM $MgCl_2$, 20 mM DTT), 8 μl T4 DNA ligase (1U/μl, Boehringer Mannheim, Indianapolis, Ind.), 8 μl diluted T7 DNA polymerase (1U/μl, New England BioLabs, Beverly, Mass.) and incubating at 37° C. for 30 min. The reaction was stopped with 300 μl of mutagenesis stop buffer (10 mM Tris pH 8.0, 10 mM EDTA).

The mutagenesis DNA was extracted once with equilibrated phenol (pH>8):chloroform:isoamyl alcohol (50:49:1), once with chloroform:isoamyl alcohol (49:1), and the DNA was ethanol precipitated at −20° C. for at least 30 min. The DNA was pelleted and the supernatant carefully removed as described above. The sample was briefly spun again and all traces of ethanol removed with a pipetman. The pellet was dried in vacuo. The DNA was resuspended in 4 μl of sterile water.

One μl mutagenesis DNA (500 ng) was transferred into 40 μl electrocompetent *E. coli* DH12S (Gibco/BRL, Gaithersburg, Md.) using the electroporation conditions in Example 9. The transformed cells were mixed with 1.0 ml 2×YT broth (Sambrook et al., supra) and transferred to 15 ml sterile culture tubes. The first round antibody phage was made by shaking the cultures overnight at 23° C. and 300 rpm. The efficiency of the electroporation was measured by plating 10 μl of $10^{-3}$ and $10^{-4}$ dilutions of the cultures on LB agar plates (see Example 12). These plates were incubated overnight at 37° C. The efficiency was determined by multiplying the number of plaques on the $10^{-3}$ dilution plate by $10^5$ or multiplying the number of plaques on the $10^{-4}$ dilution plate by $10^6$. The overnight cultures from the electroporations were transferred to 1.5 ml tubes, and the cells were pelleted by centrifuging at 14 krpm for 5 min. The supernatant, which is the first round of antibody phage, was then transferred to 15 ml sterile centrifuge tubes with plug seal caps.

Example 9

Transformation of *E. coli* by Electroporation

The electrocompetent *E. coli* cells were thawed on ice. DNA was mixed with 20–40 μL electrocompetent cells by gently pipetting the cells up and down 2–3 times, being careful not to introduce an air bubble. The cells were transferred to a Gene Pulser cuvette (0.2 cm gap, BioRAD, Hercules, Calif.) that had been cooled on ice, again being careful not to introduce an air bubble in the transfer. The cuvette was placed in the *E. coli* Pulser (BioRAD, Hercules, Calif.) and electroporated with the voltage set at 1.88 kV according to the manufacturer's recommendation. The transformed sample was immediately diluted to 1 ml with 2×YT broth and processed as procedures dictated.

Example 10

Preparation of Biotinylated Antigens and Biotinylated Antibodies

Crude *Cryptosporidium* soluble antigen (1 mg/mL, Example 1A) was extensively dialyzed into BBS. After dialysis, the protein was reacted with biotin-XX-NHS ester (Molecular Probes, Eugene, Oreg., stock solution at 40 mM in dimethylformamide) at a final concentration of 0.5 mM. The reaction was incubated at room temperature for 90 min. After 90 min, the protein was dialyzed extensively against BBS at 2–8° C. After dialysis, the biotin concentration was $5 \times 10^{-5}$ M. The biotin concentration can be measured using the HABA reagent kit (Pierce, Rockford, Ill.). The biotinylated crude *Cryptosporidium* soluble antigen was stored at $-80°$ C.

Antibodies were reacted with 3-(N-maleimidylpropionyl)biocytin using a free cysteine at the carboxy terminus of the heavy chain. The cysteine was reduced by adding DTT to a final concentration of 1 mM for 30 min at room temperature. The antibody was passed through a Sephadex G50 desalting column equilibrated in column buffer. 3-(N-maleimidylpropionyl)biocytin was added to a final concentration of 1 mM. Reactions were allowed to proceed at room temperature for 60 min. Antibodies were dialyzed extensively into BBS and stored at 2–8° C.

Example 11

Preparation of Avidin Magnetic Latex

The magnetic latex (Estapor, 10% solids, Bangs Laboratories, Fishers, Ind.) was thoroughly resuspended and 2 ml aliquoted into a 15 ml conical tube. The magnetic latex was suspended in 12 ml distilled water and separated from the solution for 10 min using a magnet (PerSeptive Biosystems, Framingham Mass.). While maintaining the separation of the magnetic latex with the magnet, the liquid was carefully removed using a 10 ml sterile pipette. This washing process was repeated an additional three times. After the final wash, the latex was resuspended in 2 ml of distilled water. In a separate 50 ml conical tube, 10 mg of avidin-HS (NeutrAvidin, Pierce, Rockford, Ill.) was dissolved in 18 ml of 40 mM Tris, 0.15 M sodium chloride, pH 7.5 (TBS). While vortexing, the 2 ml of washed magnetic latex was added to the diluted avidin-HS and the mixture vortexed an additional 30 seconds. This mixture was incubated at 45° C. for 2 hr, shaking every 30 minutes. The avidin magnetic latex was separated from the solution using a magnet and washed three times with 20 ml BBS as described above. After the final wash, the latex was resuspended in 10 ml BBS and stored at 4° C.

Immediately prior to use, the avidin magnetic latex was equilibrated in panning buffer (40 mM TRIS, 150 mM NaCl, 20 mg/ml BSA, 0.1% Tween 20 (Fisher Scientific, Pittsburgh, Pa.), pH 7.5). The avidin magnetic latex needed for a panning experiment (200 μl/sample) was added to a sterile 15 ml centrifuge tube and brought to 10 ml with panning buffer. The tube was placed on the magnet for 10 min to separate the latex. The solution was carefully removed with a 10 ml sterile pipette as described above. The magnetic latex was resuspended in 10 ml of panning buffer to begin the second wash. The magnetic latex was washed a total of 3 times with panning buffer. After the final wash, the latex was resuspended in panning buffer to the starting volume.

Example 12

Plating M13 Phage or Cells Transformed with Antibody Phage-Display Vector Mutagenesis Reaction The phage samples were added to 200 μL of an overnight culture of *E. coli* XL1-Blue when plating on 100 mm LB agar plates or to 600 μL of overnight cells when plating on 150 mm plates in sterile 15 ml culture tubes. After adding LB top agar (3 ml for 100 mm plates or 9 ml for 150 mm plates, top agar stored at 55° C., Appendix A1, Sambrook et al., supra.), the mixture was evenly distributed on an LB agar plate that had been pre-warmed (37° C.–55° C.) to remove any excess moisture on the agar surface. The plates were cooled at room temperature until the top agar solidified. The plates were inverted and incubated at 37° C. as indicated.

Example 13

Developing Nitrocellulose Filters with Alkaline Phosphatase Conjugates

After overnight incubation of nitrocellulose filters on the LB agar plates, the filters were carefully removed from the plates with membrane forceps and incubated for 2 hr in block. After 2 hr, the filters were incubated with goat anti-mouse kappa-AP (Southern Biotechnology Associates, Inc, Birmingham, Ala.) for 2–4 hours. The goat anti-mouse kappa-AP was diluted into block at a final concentration of 1 μg/ml. Filters were washed three times with 40 mM TRIS, 150 mM NaCl, 0.05% Tween 20, pH 7.5 (TBST) (Fisher Chemical, Pittsburgh, Pa.) for 5 min each. After the final wash, the filters were developed in a solution containing 0.2 M 2-amino-2-methyl-1-propanol (JBL Scientific, San Luis Obispo, Calif.), 0.5 M TRIS, 0.33 mg/ml nitro blue tetrazolium ((NBT) Fisher Scientific, Pittsburgh, Pa.) and 0.166 mg/ml 5-bromo-4-chloro-3-indolyl-phosphate, p-toluidine salt.

Example 14

Selection of Polyclonal Antibodies to Crude Soluble *Cryptosporidium* Antigen The first round antibody phage was prepared as described in Example 8 using BS45 uracil template. Electroporations of mutagenesis DNA were performed yielding phage samples derived from different immunized mice. To create more diversity in the polyclonal library, each phage sample was panned separately. The antibody phage (about 0.9 mL) from each electroporation was transferred to a 15 mL disposable sterile centrifuge tube with a plug seal cap. BSA (30 μL of 300 mg/mL solution) and 1 M Tris (50 μL of 1 M stock solution, pH 8.0) were added to each phage stock. Ten μL of $3 \times 10^{-6}$ M biotinylated crude *Cryptosporidium* soluble antigen was added to each phage sample (Example 1A). The antibody phage were allowed to come to equilibrium with the antigen-biotin by incubating the phage at 2–8° C. overnight.

After the incubation, the phage samples were panned with avidin magnetic latex. The equilibrated avidin magnetic latex (see Example 11), 200 μL latex per sample, was incubated with the phage for 10 min at room temperature. After 10 min, approximately 9 mL of panning buffer was added to each phage sample, and the magnetic latex was separated from the solution using a magnet. After a ten minute separation, the unbound phage was carefully removed using a 10 mL sterile pipette. The magnetic latex was then resuspended in 10 mL of panning buffer to begin the second wash. The latex was washed a total of four times as described above. For each wash, the tubes were in contact with the magnet for 10 min to separate unbound phage from the magnetic latex. After the fourth wash, the magnetic latex was resuspended in 1 mL of panning buffer and transferred to a 1.5 mL tube.

The entire volume of magnetic latex for each sample was then resuspended in 200 mL 2YT and was plated on 150 mm LB plates as described in Example 12. The 150 mm plates were used to amplify the phage binding to the magnetic latex to generate the next round of antibody phage. These plates were incubated at 37° C. for 4 hr, then overnight at 20° C. After the overnight incubation, the second round antibody phage was eluted from the 150 mm plates by pipetting 10 mL 2YT media onto the lawn and gently shaking the plate at room temperature for 20 min. The phage samples were transferred to 15 mL disposable sterile centrifuge tubes with a plug seal cap, and the debris from the LB plate was pelleted by centrifuging the tubes for 15 min at 3500 rpm. The second round antibody phage was then transferred to a new tube.

The second round of panning was set up by diluting 50 µL of each phage stock into 950 µL panning buffer in 15 mL disposable sterile centrifuge tubes with plug seal cap. The biotinylated *Cryptosporidium* antigen was added to each sample as described for the first round of panning, and the phage samples were incubated overnight at 2–8° C. The phage samples were panned with avidin magnetic latex following the overnight incubation as described above. After washing the latexes with panning buffer, each latex was plated on 150 mm LB agar plates. The plates were incubated at 37° C. for 4 hr, then overnight at 20° C. The third round antibody phage was eluted as described above.

Panning was continued by diluting phage samples into panning buffer as described above or by enriching the phage samples by panning using 7F11 magnetic latex (described in Examples 21 and 22 of U.S. Pat. No. 6,555,310, issued Apr. 29, 2003) prior to functional panning (see, Example 16 of U.S. Pat. No. 6,555,310). The progress of panning was measured by plating aliquots of each latex sample on 100 mm LB agar plates to determine the percentage of kappa positives. The majority of latex from each panning (99%) was plated on 150 mm LB agar plates to amplify the phage binding to the latex (see above). The 100 mm LB agar plates were incubated at 37° C. for 6–7 hr, after which the plates were transferred to room temperature and nitrocellulose filters (pore size 0.45 mm, BA85 Protran, Schleicher and Schuell, Keen, N.H.) were overlayed onto the plaques. Plates with nitrocellulose filters were incubated overnight at room temperature.

After the overnight incubation, the next round antibody phage was eluted from the 150 mm plates, and the filters were developed with goat anti-mouse kappa alkaline phosphatase as described in Example 13. Individual phage samples having kappa positive percentages of greater than 80% on plaque lifts were pooled. The pooled phage was subcloned into the expression vector, pBRncoH3. The subcloning was done generally as described in Example 18 of U.S. Pat. No. 6,555,310.

Example 15

Expression and Purification of Recombinant Antibodies and PDI Antigen

This Example describes the expression of PDI, and recombinant antibodies that bind to PDI, using recombinant *E. coli* cells that contain genes encoding the PDI antigen of *Cryptosporidium parvum* or antibodies against this antigen.

A. Expression and Purification of Recombinant Antibodies

A shake flask inoculum was generated overnight from a −70° C. cell bank in an Innova 4330 incubator shaker (New Brunswick Scientific, Edison, N.J.) set at 37° C., 300 rpm. The inoculum was used to seed a 20 L fermentor (Applikon, Foster City, Calif.) containing defined culture medium (Pack et al. (1993) *Bio/Technology* 11: 1271–1277) supplemented with 3 g/L L-leucine, 3 g/L L-isoleucine, 12 g/L casein digest (Difco, Detroit, Mich.), 12.5 g/L glycerol and 10 µg/ml tetracycline. The temperature, pH and dissolved oxygen in the fermentor were controlled at 26° C., 6.0–6.8 and 25% saturation, respectively. Foam was controlled by addition of polypropylene glycol (Dow, Midland, Mich.). Glycerol was added to the fermentor in a fed-batch mode. Fab expression was induced by addition of L(+)-arabinose (Sigma, St. Louis, Mo.) to 2 g/L during the late logarithmic growth phase. Cell density was measured by optical density at 600 nm in an UV-1201 spectrophotometer (Shimadzu, Columbia, Md.). Following run termination and adjustment of pH to 6.0, the culture was passed twice through an M-210B-EH Microfluidizer (Microfluidics, Newton, Mass.) at 17000 psi. The high pressure homogenization of the cells released the Fab into the culture supernatant.

The first step in purification was expanded bed immobilized metal affinity chromatography (EB-IMAC). Streamline™ chelating resin (Pharmacia, Piscataway, N.J.) was charged with 0.1 M $NiCl_2$ and was then expanded and equilibrated in 50 mM acetate, 200 mM NaCl, 10 mM imidazole, 0.01% $NaN_3$, pH 6.0 buffer flowing in the upward direction. A stock solution was used to bring the culture homogenate to 10 mM imidazole, following which it was diluted two-fold or higher in equilibration buffer to reduce the wet solids content to less than 5% by weight. It was then loaded onto the Streamline column flowing in the upward direction at a superficial velocity of 300 cm/hr. The cell debris passed through unhindered, but the Fab was captured by means of the high affinity interaction between nickel and the hexahistidine tag on the Fab heavy chain. After washing, the expanded bed was converted to a packed bed and the Fab was eluted with 20 mM borate, 150 mM NaCl, 200 mM imidazole, 0.01% $NaN_3$, pH 8.0 buffer flowing in the downward direction.

The second step in the purification used ion-exchange chromatography (IEC). Q Sepharose FastFlow resin (Pharmacia, Piscataway, N.J.) was equilibrated in 20 mM borate, 37.5 mM NaCl, 0.01% $NaN_3$, pH 8.0. The Fab elution pool from the EB-IMAC step was diluted four-fold in 20 mM borate, 0.01% $NaN_3$, pH 8.0 and loaded onto the IEC column. After washing, the Fab was eluted with a 37.5–200 mM NaCl salt gradient. The elution fractions were evaluated for purity using an Xcell II™ SDS-PAGE system (Novex, San Diego, Calif.) prior to pooling. Finally, the Fab pool was concentrated and diafiltered into 20 mM borate, 150 mM NaCl, 0.01% $NaN_3$, pH 8.0 buffer for storage. This was achieved in a Sartocon Slice™ system fitted with a 10,000 MWCO cassette (Sartorius, Bohemia, N.Y.). The final purification yields were typically 50%. The concentration of the purified Fab was measured by UV absorbance at 280 nm, assuming an absorbance of 1.6 for a 1 mg/ml solution.

B. Expression and Purification of PDI

A shake flask inoculum was generated overnight from a −70° C. cell bank in an incubator shaker set at 37° C., 300 rpm. The cells were cultured in a defined medium described above. The inoculum was used to seed a 2 L Tunair shake flask (Shelton Scientific, Shelton, Conn.) which was grown at 37° C., 300 rpm. Expression was induced by addition of L(+)-arabinose to 2 g/L during the logarithmic growth phase, following which, the flask was maintained at 23° C., 300 rpm. Following batch termination, the culture was passed through an M-110Y Microfluidizer (Microfluidics, Newton, Mass.) at 17000 psi. The homogenate was clarified in a J2-21 centrifuge (Beckman, Fullerton, Calif.).

Purification employed immobilized metal affinity chromatography. Chelating Sepharose FastFlow™ resin (Pharmacia, Piscataway, N.J.) was charged with 0.1 M $NiCl_2$ and equilibrated in 20 mM borate, 150 mM NaCl, 10 mM imidazole, 0.01% $NaN_3$, pH 8.0 buffer. A stock solution was used to bring the culture supernatant to 10 mM imidazole and 2-mercaptoethanol was added to 1 mM. The culture supernatant was then mixed with the resin and incubated in the incubator shaker set at room temperature, 150–200 rpm. The antigen was captured by means of the high affinity interaction between nickel and the hexahistidine tag on the antigen. The culture supernatant and resin mixture is poured into a chromatography column. After washing, the antigen was eluted with 20 mM borate, 150 mM NaCl, 200 mM imidazole, 1 mM 2-mercaptoethanol, 0.01% $NaN_3$, pH 8.0 buffer. The antigen pool was concentrated in a stirred cell fitted with a 10,000 MWCO membrane (Amicon, Beverly, Mass.). It was then dialyzed overnight into 20 mM borate, 150 mM NaCl, 0.01% $NaN_3$, pH 8.0 for storage, using 12–14,000 MWCO dialysis tubing. The purified antigen was evaluated for purity by SDS-PAGE analysis. The concentration of the PDI antigen is measured by UV absorbance at 280 nm, assuming an absorbance of 0.66 for a one mg/ml solution.

Example 16

Selection of Monoclonal Antibodies to Crude Cryptosporidium Antigen from the Polyclonal Antibody It was desired to have a monoclonal/polyclonal antibody pair to one specific antigen. Individual colonies were picked off the LB agar tetracycline plates from the subcloned phage plated in Example 14 into 2YT media and tetracycline (10 µg/mL). The cultures were grown overnight at 37° C., 300 rpm. These monoclonal antibodies were expressed and purified as described in Example 15, and biotinylated as described in Example 10. The polyclonal antibody (Example 14) was conjugated to alkaline phosphatase as described in Example 19.

The sensitivity of the monoclonal antibodies was determined by performing a sandwich assay using the biotinylated monoclonal antibodies and the alkaline phosphatase-conjugated polyclonal antibodies. Assays were performed with streptavidin coated plates such as Reacti-Bind™ streptavidin coated polystyrene 96 well plates (Pierce Chemical, Rockford, Ill.). After washing the 96 well plate with a plate washer such as the Skan Washer (Skatron Instruments, Sterling, Va.), biotinylated monoclonal antibody (50 µL of 2.5 µg/mL stock diluted in block) was added to 8 wells. The plate was incubated at room temperature for 1 hr. The plate was then washed, after which Cryptosporidium soluble antigen (50 µL) was added in duplicate to the biotinylated monoclonal wells at different concentrations. The approximate concentrations of crude antigen were 5 µg/mL, 0.5 µg/mL, 0.05 µg/mL, and 0. Antigen was incubated for 1 hr at room temperature, after which the plate was washed. The polyclonal antibody-alkaline phosphatase conjugate (50 µL of 2.5 µg/mL diluted in block) was added and incubated at room temperature for 1 hr.

After 1 hr, the plate was washed and developed using the ELISA Amplification System (Gibco BRL, Gaithersburg, Md.) according to the manufacturer's instructions. Monoclonal antibody CP.2 had the highest signal, which was slightly above background at 0.05 µg/mL. This monoclonal was chosen to make a complementary polyclonal, and the monoclonal was used to screen a Cryptosporidium cDNA library to identify the antigen.

Example 17

Selection and Cloning of Polyclonal Antibody Complementary to CP.2 Monoclonal Antibody Phage samples enriched for binding to crude Cryptasporidium antigen as described in Example 14 were pooled using an equal number of phage from each sample. Biotinylated CP.2 monoclonal antibody (12 µl, $10^{-6}$ M) and soluble crude Cryptosporidium antigen (12 µl, about 2 mg/mL) were mixed and incubated for 10 min at room temperature. Twenty µl of CP.2 biotin/antigen was added to the phage sample, and the sample was incubated overnight at 2–8° C. The sample was panned with avidin magnetic latex and plated as described in Example 14. The eluted phage was pawed a second time as described using biotinylated CP.2/crude Cryptosporidium antigen. The phage eluted after the second round of panning were subcloned as described in Example 18 of U.S. Pat. No 6,555,310. This polyclonal was designated SCPc.4.PC.

Example 18

Microtiter Plate Assay Sensitivity

The sensitivity of the monoclonal/polyclonal antibody pair was determined with a sandwich assay using biotinylated CP.2 and alkaline phosphatase conjugated SCPc.4.PC. After washing the 96 well plate with a plate washer (see Example 16), biotinylated CP.2 (50 µL of 2.5 µg/mL diluted in block) was added to 12 wells. The plate was incubated at room temperature for 1 hr. The plate was washed, then purified PDI (50 µL) was added in duplicate to the biotinylated monoclonal wells at five different concentrations of antigen (see Table 3) and block was added to the last two wells for the blank. Antigen was incubated for 1 hr at room temperature, after which the plate was washed. The complementary polyclonal alkaline phosphatase conjugate (SCPc.4.PC, 50 µL of 2.5 µg/mL diluted in block) was added and incubated at room temperature for 1 hr. After 1 hr, the plate was washed and developed using the ELISA Amplification System according to the manufacturer's instructions. The signal was read at 490 nm using a microplate reader (Molecular Devices, Sunnyvale, Calif.). Table 3 lists the signal at 490 nm versus the concentration of PDI antigen.

TABLE 3 concentration of PDI antigen versus signal at 490 nm (endpoint reading) for the antibody pair CP.2/SCPc.4.PC

| Concentration (ng/mL) | Absorbance (490 nm) |
|---|---|
| 0 | 0.055 |
| 3.1 | 0.71 |
| 6.25 | 1.203 |
| 12.5 | 2.07 |
| 25 | 2.687 |
| 50 | 2.996 |

Example 19

Preparation and Testing of Device for Detecting C. parvum Infection

This Example describes the preparation and testing of a device for detecting *Cryptosporidium parvum* infection. The device employs the recombinant polyclonal antibody to immobilize *C. parvum* PDI on a solid support, and a recombinant monoclonal antibody to detect the presence of immobilized PDI.

A. Preparation of Antibody-Alkaline Phosphatase Conjugates for Use as Detection Reagents.

Detection reagents for use in the assay were prepared by conjugating alkaline phosphatase to antibodies for protein disulfide isomerase. The recombinant monoclonal antibody CP.2 was used to detect protein disulfide isomerase. Alkaline phosphatase (AP, Calzyme Laboratories, San Luis Obispo, Calif.) was dialyzed against a minimum of 100 volumes of column buffer (50 mM potassium phosphate, 10 mM sodium, 150 mM NaCl, 1 mM $MgSO_4$, pH 7.0) at 2–8° C. for a minimum of four hours and the buffer was changed at least twice prior to use of the AP. After the AP was removed from dialysis and brought to room temperature, the concentration was determined by determining the $A_{280}$, with an absorbance of 0.77 indicating a 1 mg/ml solution. The AP was diluted to 5 mg/ml with column buffer.

For crosslinking the AP to the antibody, AP was first linked to succinimidyl 4-(N-maleimidomethyl cyclohexane-1-carboxylate (SMCC, Pierce Chemical Co., Rockford Ill.) using a 20:1 ratio of SMCC:AP. SMCC was dissolved in acetonitrile at 20 mg/ml and diluted by a factor of 84 when added to AP while vortexing or rapidly stirring. The solution was allowed to stand at room temperature for 90 minutes before the unreacted SMCC and low molecular weight reaction products were separated from the AP using gel filtration chromatography (G-50 Fine, Pharmacia Biotech, Piscataway, N.J.) in a column equilibrated with column buffer.

Recombinant antibodies were reacted with 1 mM dithiothreitol (DTT, Calbiochem, San Diego, Calif.) for 30 minutes at room temperature to reduce a cysteine residue present near the carboxy terminus of the heavy chain constant region. The DTT was separated from the antibody by gel filtration chromatography using G50 Fine in column buffer without $MgSO_4$ but containing 0.1 mM ethylenediaminetetraacetic acid (EDTA, Fisher Scientific, Pittsburgh, Pa.). The AP and the antibody were mixed together in a molar ratio of 6 antibodies to one alkaline phosphatase and the conjugation reaction was allowed to continue for one hour at room temperature. To stop the conjugation, 2-mercaptoethanol was added to 1 mM final concentration to the conjugate solution and reacted for 5 minutes followed by the addition of N-ethyl maleimide to 2 mM final concentration. The conjugate was purified by gel filtration chromatography using SEPHACRYL™ S-200 HR (Pharmacia Biotech, Piscataway, N.J.). The free antibody was excluded from the conjugate pool which was diluted for use in immunoassays in a conjugate diluent containing 1% bovine serum albumin (from 30% BSA, Bayer, Kankakee. Ill.), 2% casein (Hammersten grade, Research Organics, Cleveland, Ohio), 100 mM trehalose (Aldrich Chemical Co., Milwaukee, Wis.), 50 mM potassium phosphate, 150 mM sodium chloride, 1 mM $MgSO_4$, 0.1 mM $ZnCl_2$, 0.1% polyvinyl alcohol (80% hydrolyzed, Aldrich Chemical Co., Milwaukee Wis.), pH 7.0.

B. Preparation of Antibody-Casein Conjugates for Use as Capture Reagents

Capture reagents for protein disulfide isomerase were prepared as follows. Where recombinant antibodies were used as anchor moieties, the antibodies were first conjugated to casein. Casein was dissolved in deionized water at 2.5% solids by stirring it at 37–45° C. while adding concentrated potassium hydroxide to keep the pH of the solution between 7 and 8. After the pH had stabilized at 7.0, the casein was diluted with deionized water to a final $A_{280}$ of 10. The casein solution was subjected to tangential flow filtration through an ultrafiltration membrane with a molecular weight cut-off of 300,000 in order to exclude aggregated protein from the filtrate. The casein filtrate was concentrated to a final $A_{280}$ of approximately 10 by ultrafiltration. A solution of SMCC was prepared at 20 mg/ml (60 mM) in acetonitrile; this was diluted into the casein solution to a final concentration of 2 mM SMCC. The solution was allowed to stand for 90 minutes at room temperature and then was subjected to gel filtration chromatography in a column containing G50 Fine equilibrated in column buffer in order to separate the protein from the reactants. The casein was mixed with recombinant antibody SCPc.4.PC that had been reacted with 1 mM DTT and subjected to gel filtration chromatography to remove the DTT as described in Example 19A above. The antibody was mixed with the casein in a 4:1 molar ratio and the reaction was allowed to proceed for one hour at room temperature before the conjugation was stopped as described above. The conjugate solution was subjected to gel filtration chromatography in a column containing SEPHACRYL™ S-200 HR in order to separate the conjugated antibody from the unconjugated antibody. The conjugated antibody was concentrated using an ultrafiltration membrane and subjected to dialysis vs. borate-buffered saline (BBS, 20 mM borate, 150 mM sodium chloride, 0.02% sodium azide, pH 8.2) and stored in BBS until immobilization on nylon membranes.

C. Preparation of Assay Devices

The assays were performed using capture reagents that were immobilized on nylon membranes. Recombinant Fab antibodies were conjugated to casein as described above prior to immobilization. The antibodies were immobilized on the nylon membranes (5 µm pore size; IMMUNODYNE™, Pall Corporation, Glen Cove, N.Y.) in a continuous process by pumping an antibody solution directly onto the membrane while the membrane was moved past a stationary nozzle which dispensed the antibody solution at a flow rate controlled by the pump. The antibody solution typically contained antibody at a concentration between 1 and 5 mg/ml in a buffer containing 20 mM borate, 150 mM sodium chloride, 0.02% sodium azide, and 10% trehalose, pH 8.2.

Each antibody was immobilized in a line approximately 0.040 inches wide, such that approximately 36 μL of antibody solution was required per linear foot of membrane. The antibody solution applied to the membrane was dried prior to blocking the entire membrane by saturating it with a solution containing 2% casein, 40% STABILICOAT™ (Bio-metric Systems, Eden Prairie, Minn.), 0.25% TRITON X-100™ (Sigma Chemical Co., St. Louis, Mo.) and drying the membrane in a drying tunnel or in a dry room. The antibody can also be applied in spots by applying a volume of approximately 1 μL of antibody solution to the membrane at the desired location prior to blocking and drying the membrane. Generally, several lines of immobilized antibody were placed on a membrane in this manner and the membrane was cut perpendicular to the direction of the antibody lines for placement in the assay devices.

Figure 2B:
Figure 2C:
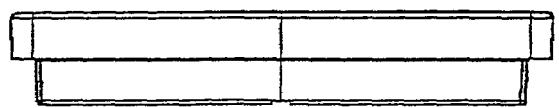

The cut membrane pieces were ultrasonically welded to an opening in a plastic device top (see FIG. 1A—top view, FIG. 1B—side section, and FIG. 1C—end view) which was then ultrasonically welded to a plastic bottom piece (see FIG. 2A—top view, FIG. 2B—side section, and FIG. 2C—end view) having grooves cut into its upper surface. The contact between the membrane and the two plastic pieces resulted in a network of capillary channels that caused fluids added to the membrane to flow through the membrane and into the capillary network between the two plastic pieces. Such devices are described in European Patent Application No. 447154.

For the immunoassay of protein disulfide isomerase, a total of three lines of antibody were immobilized on the membrane. The top line in the device was a positive control for the immunoassay of protein disulfide isomerase. The antibody solution used in the immobilization step for the positive control contained protein disulfide isomerase at approximately 1 μg/ml mixed with the SCPc.4.PC-casein conjugate at approximately 1 mg/ml. The next line on the membrane was for the capture and detection of protein disulfide isomerase. The solution used to immobilize the antibody for protein disulfide isomerase contained approximately 2 mg/ml of the SCPc.4.PC antibody conjugated to casein. The last line of immobilized antibody on the device was a negative control line; the antibody solution used to apply this line to the membrane contained a recombinant polyclonal antibody (2 mg/ml) that was specific for an antigen not found in *C. parvum*.

For filtering samples prior to performing the assays, disposable filter devices were constructed using standard 10-cc plastic syringes. Disks of filter material were cut to a diameter that would allow the disk to be placed into the barrel of the syringe so that sufficient contact was created between the syringe barrel and the edge of the filter disk. This prevented fluids from bypassing the filter material when liquid samples were forced through the filter by the plunger. At the bottom of the syringe closest to the outlet was a disk of glass fiber filter (GF/F, 0.7 μm, Whatman, Clifton, N.J.) followed by a disk of porous plastic (Porex Technologies, Fairburn, Ga.). The next two disks of filter material were both cut from CELLUPORE™ filter grade 850 material (Cellulo Co., Fresno, Calif.). The next disk of filter material was cut from CELLUPORE™ filter grade 315 material (Cellulo Co., Fresno, Calif.). The uppermost filter element in the syringe barrel was a bonded cellulose acetate material (American Filtrona, Richmond, Va.) that served as a prefilter for the filter elements described previously. An alternative filter device that contains essentially the same elements is the AUTOVIAL™ (Whatman, Clifton, N.J.) which is a disposable syringe that has a GMF glass fiber filter with a rating of 0.45 μm already connected to the end of the syringe. The other filter elements described above are placed in the barrel of the AUTOVIAL™ in the same order.

D. Immunoassay of Protein Disulfide Isomerase

Stool samples (approximately 0.5 g or 0.5 ml) were diluted tenfold with sample diluent containing 1% casein, 100 mM potassium phosphate, 150 mM sodium choride, 0.1% Dow 193 surfactant (Dow Corning, Midland, Mich.), 0.1% bovine IgG (Sigma Chemical Co., St. Louis, Mo.), 0.1% sodium azide, pH 7.0, and then poured into the barrel of a filter device. The syringe plunger was inserted into the filter device and pressed down to expel the filtered sample through the end of the syringe into a tube. Using a disposable transfer pipet, 0.5 ml of sample was taken from the tube and transferred to the exposed membrane in the immunoassay device described above.

After the sample drained through the membrane in the device, the antibody CP.2 conjugated to alkaline phosphatase was applied in a volume of 140 μL and incubated for 3 minutes. The antibody conjugate concentration was approximately 10 μg/ml. After the incubation, six drops of wash solution containing 100 mM Tris (hydroxymethyl) aminomethane (TRIS, Fisher Scientific, Pittsburgh, Pa.), 150 mM sodium chloride, 0.5% Dow 193 surfactant, 0.1% sodium azide, and 20 mg/l of nitro blue tetrazolium (NBT) were applied from a dropper bottle. After the wash drained into the membrane, another six drops of wash solution were applied and allowed to drain. Three drops of substrate solution containing 10 mM indoxyl phosphate (JBL Scientific, San Luis Obispo, Calif.), 200 mM 2-amino-2-methyl-1-propanol (JBL Scientific, San Luis Obispo, Calif.), 500 mM TRIS, pH 10.2, were added from a dropper bottle and the device was incubated for five minutes at room temperature.

At the end of the incubation time, the presence of any visually detectable purple to black lines was noted. The positive control zone described above developed a clearly visible line that resulted from the binding of the antibody-alkaline phosphatase conjugate to the immobilized complex of antigen and antibody. Control samples containing protein disulfide isomerase spiked from purified preparations of recombinant protein to concentrations of 2 ng/ml or greater resulted in a visible line at the zone for the detection of this antigen. The negative control zone for the detection of non-specific binding of reagents developed a visible response for less than 1% of the clinical samples tested. When tested again using ¼ of the initial sample volume, no visible response was observed at the negative control zone for any of the samples.

E. Sensitivity of Assay with Purified Antigen

The purified recombinant antigen was serially diluted in a solution containing 1% bovine serum albumin, 10 mM 3-(N-morpholino)propanesulfonic acid (Fisher Scientific, Pittsburgh, Pa.), 150 mM sodium chloride, and 0.1% sodium azide, pH 7.0, and dilutions were tested in replicates of ten using the same procedure employed with stool samples, a tenfold dilution of a 0.5-ml sample followed by filtration of the diluted sample. The lowest concentration of the antigen that consistently produced a positive visual response at the detection zone on the membrane was determined to be the limit of sensitivity of the assay. For protein disulfide isomerase, this was found to be 3 ng/ml.

F. Clinical Sensitivity and Specificity of the Assay

The clinical sensitivity and specificity of the assay was determined by testing 444 samples obtained from a patient population in Mexico and Peru. The results were compared to those obtained with a standard ova and parasite examination and with a commercially available enzyme-labeled microtiter plate immunoassay (Alexon ProSpecT Cryptosporidium Microplate Assay). Discrepancies between methods were resolved by comparing the three results for the discrepant sample. Since no method exists that can unequivocally identify the presence of the organism in samples, when two of the three methods produced the same result that result was judged to be the correct result for that sample. Clinical sensitivity, specificity, positive predictive value and negative predictive value were calculated as described in the *Tietz Textbook of Clinical Chemistry* (second edition, page 496). The results are shown in Table 4–Table 6. The assay for protein disulfide isomerase was shown to be more sensitive than traditional ova and parasite methods for the detection of *C. parvum* in clinical samples. Furthermore, the assay of the present invention was substantially equivalent to a commercially available immunoassay that detects an unspecified antigen or mixture of antigens.

TABLE 4

|  |  | O & P Examination | | |
|---|---|---|---|---|
|  |  | + | - | Total |
| Triage® *C. parvum* | + | 53 | 7 | 60 |
|  | - | 5 | 379 | 384 |
|  | Total | 58 | 386 | 444 |
| Sensitivity |  |  | 91.4% |  |
| Sensificity |  |  | 98.2% |  |
| Positive Predictive Value |  |  | 88.3% |  |
| Negative Predictive Value |  |  | 98.7% |  |

TABLE 5

|  |  | Alexon | | |
|---|---|---|---|---|
|  |  | + | - | Total |
| Triage® *C. parvum* | + | 58 | 2 | 60 |
|  | - | 7 | 377 | 384 |
|  | Total | 65 | 379 | 444 |
| Sensitivity |  |  | 89.2% |  |
| Sensificity |  |  | 99.5% |  |
| Positive Predictive Value |  |  | 96.7% |  |
| Negative Predictive Value |  |  | 98.2% |  |

TABLE 6

|  |  | Resolved | | |
|---|---|---|---|---|
|  |  | + | - | Total |
| Triage® *C. parvum* | + | 59 | 1 | 60 |
|  | - | 5 | 379 | 384 |
|  | Total | 64 | 380 | 444 |
| Sensitivity |  |  | 92.2% |  |
| Sensificity |  |  | 99.7% |  |
| Positive Predictive Value |  |  | 98.3% |  |
| Negative Predictive Value |  |  | 98.7% |  |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A method of diagnosing infection of a mammal by a *Cryptosporidium* species, the method comprising:
   contacting a stool sample obtained from the mammal with a capture reagent comprising an antibody which binds to *Cryptosporidium* protein disulfide isomerase, wherein the capture reagent forms a complex with the protein disulfide isomerase if the protein disulfide isomerase is present in the stool sample; and
   detecting whether protein disulfide isomerase is bound to the capture reagent, wherein the presence of protein disulfide isomerase in indicative of *Cryptosporidium* infection of the mammal.

2. The method of claim 1, wherein the capture reagent comprises an antibody that specifically binds to the amino acid sequence AWFCGTNEDFAKYAS-NIRKVAADYREKYAFVF (SEQ ID NO: 3).

3. The method of claim 2, wherein the capture reagent comprises an antibody that specifically binds to the amino acid sequence of SEQ ID NO: 2.

4. The method of claim 1 wherein the antibody is a recombinant antibody.

5. The method of claim 4, wherein the antibody is a recombinant polyclonal antibody.

6. The method of claim 1, where in the capture reagent is immobilized on a solid support.

7. The method of claim 6, wherein the capture reagent is immobilized on the solid support prior to contacting the capture reagent with the test sample.

8. The method of claim 1, wherein the detection of the protein disulfide isomerase is performed by contacting the protein disulfide isomerase with a detection reagent which binds to the protein disulfide isomerase.

9. The method of claim 8, wherein the detection reagent comprises an antibody which binds to protein disulfide isomerase.

10. The method of claim 8, wherein the detection reagent comprises a detectable label.

11. The method of claim 10, wherein the detectable label is selected from the group consisting of a radioactive label, a fluorophore, a dye, an enzyme, and a chemiluminescent label.

12. A kit for diagnosing infection of a mammal by a *Cryptosporidium* species, the kit comprising;
   a solid support upon which is immobilized a capture reagent in antibody which binds to a protein disulfide isomerase of *Cryptosporidium parvum*; and
   a detection reagent comprising an antibody which binds to the protein disulfide isomerase.

13. The kit according to claim 12, wherein the kit further comprises a positive control that comprises a protein disulfide isomerase.

14. The kit according to claim 13, wherein the capture reagent comprises an antibody that specifically binds to the amino acid sequence AWFCGTNEDFAKYAS-NIRKVAADYREKYAFVF (SEQ ID NO: 3).

15. The method of claim 1, wherein the antibody is an antibody fragment.

16. The kit of claim 12, wherein at least one of the capture reagent antibody or the detection reagent antibody is an antibody fragment.

* * * * *

UNITED STATES PATENT AND TRADEMARK OFFICE
CERTIFICATE OF CORRECTION

PATENT NO. : 7,052,858 B2  Page 1 of 1
APPLICATION NO. : 09/877933
DATED : May 30, 2008
INVENTOR(S) : Gray et al.

It is certified that error appears in the above-identified patent and that said Letters Patent is hereby corrected as shown below:

Title page, item (75) Inventors: Delete lines 3-5, insert -- (US); Joseph Buechler, Carlsbad, CA (US) --.

Title page, item (73) Assignee: Delete lines 2-4, insert -- CA (US) --.

Title page, item (*) Notice: Delete lines 3-5, insert -- U.S.C. 154(b) by 666 days --.

Signed and Sealed this

Ninth Day of June, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,052,858 B2 | Page 1 of 1 |
| APPLICATION NO. | : 09/877933 | |
| DATED | : May 30, 2006 | |
| INVENTOR(S) | : Joseph Buechler et al. | |

It is certified that error appears in the above-identified patent and that said Letters Patent is hereby corrected as shown below:

Title Pg,

In item (75) Inventors:

Please change Inventor name "Joe Buechler" to -- Joseph Buechler --.

Signed and Sealed this

Twenty-third Day of June, 2009

JOHN DOLL
*Acting Director of the United States Patent and Trademark Office*

UNITED STATES PATENT AND TRADEMARK OFFICE
CERTIFICATE OF CORRECTION

PATENT NO.          : 7,052,858 B2
APPLICATION NO.  : 09/877933
DATED                  : May 30, 2006
INVENTOR(S)         : Gray et al.

Page 1 of 1

It is certified that error appears in the above-identified patent and that said Letters Patent is hereby corrected as shown below:

Title page, item (75) Inventors: Delete lines 3-5, insert -- (US); Joseph Buechler, Carlsbad, CA (US) --.

Title page, item (73) Assignee: Delete lines 2-4, insert -- CA (US) --.

Title page, item (*) Notice: Delete lines 3-5, insert -- U.S.C. 154(b) by 666 days --.

This certificate supersedes the Certificate of Correction issued June 9, 2009.

Signed and Sealed this

Seventh Day of July, 2009

JOHN DOLL
*Acting Director of the United States Patent and Trademark Office*

SEQUENCE LISTING

```
<160> NUMBER OF SEQ ID NOS: 19

<210> SEQ ID NO 1
<211> LENGTH: 1446
<212> TYPE: DNA
<213> ORGANISM: Cryptosporidium parvum
<220> FEATURE:
<221> NAME/KEY: CDS
<222> LOCATION: (1)..(1446)
<223> OTHER INFORMATION: C. parvum protein disulfide isomerase (PDI)
      cDNA of Applicants

<400> SEQUENCE: 1 atg atc gga att aga agc ttg gtt tca gca gca ttt tta ggt ttt tct      48
Met Ile Gly Ile Arg Ser Leu Val Ser Ala Ala Phe Leu Gly Phe Ser
  1               5                  10                  15 tgt ctc tcc aag gta gtc ttg ggt gga gat gaa gct cac ttc att tca      96
Cys Leu Ser Lys Val Val Leu Gly Gly Asp Glu Ala His Phe Ile Ser
             20                  25                  30 gaa cac att act tcc tta act tcc tcc aac ttc gaa gac ttc att aag     144
```

-continued

```
          Glu His Ile Thr Ser Leu Thr Ser Ser Asn Phe Glu Asp Phe Ile Lys
              35                  40                  45 agc aag gaa cac gta att gtt act ttc ttt gcc cca tgg tgc ggc cat              192
Ser Lys Glu His Val Ile Val Thr Phe Phe Ala Pro Trp Cys Gly His
 50                  55                  60 tgt act gct tta gag cca gaa ttc aag gca aca tgc gct gaa atc tca              240
Cys Thr Ala Leu Glu Pro Glu Phe Lys Ala Thr Cys Ala Glu Ile Ser
 65                  70                  75                  80 aag ctc tct ccc cca gta cac tgt ggc agt gtt gat gca act gaa aat              288
Lys Leu Ser Pro Pro Val His Cys Gly Ser Val Asp Ala Thr Glu Asn
                 85                  90                  95 atg gag ctt gca caa caa tat ggt gtg agc gga tac cca acc atc aaa              336
Met Glu Leu Ala Gln Gln Tyr Gly Val Ser Gly Tyr Pro Thr Ile Lys
            100                 105                 110 ttc ttc agt ggt att gac agt gtt cag aac tat tca gga gca aga agc              384
Phe Phe Ser Gly Ile Asp Ser Val Gln Asn Tyr Ser Gly Ala Arg Ser
            115                 120                 125 aag gat gca ttc atc aag tat att aag aag ttg acc gga cca gca gtc              432
Lys Asp Ala Phe Ile Lys Tyr Ile Lys Lys Leu Thr Gly Pro Ala Val
130                 135                 140 caa gtt gct gaa tca gaa gaa gct atc aag aca atc ttc gct tct tct              480
Gln Val Ala Glu Ser Glu Glu Ala Ile Lys Thr Ile Phe Ala Ser Ser
145                 150                 155                 160 tct tca gcc ttt gtt gga aga ttc acc tct aag gac tca gct gag tat              528
Ser Ser Ala Phe Val Gly Arg Phe Thr Ser Lys Asp Ser Ala Glu Tyr
                165                 170                 175 gct gtc ttc gag aag gtt gct agt ggt cac cgc gag cac aac tat gct              576
Ala Val Phe Glu Lys Val Ala Ser Gly His Arg Glu His Asn Tyr Ala
            180                 185                 190 ttc att gct ttc ttc caa gaa ggt gaa caa aag ctc gag gta tta cac              624
Phe Ile Ala Phe Phe Gln Glu Gly Glu Gln Lys Leu Glu Val Leu His
            195                 200                 205 aag gac gag gag cca gtt tct ctc cca atg cca aag act gtt gaa gag              672
Lys Asp Glu Glu Pro Val Ser Leu Pro Met Pro Lys Thr Val Glu Glu
210                 215                 220 ttg gag gcc aag ata tcc ata atg aat gta cca ttg ttc tct gca att              720
Leu Glu Ala Lys Ile Ser Ile Met Asn Val Pro Leu Phe Ser Ala Ile
225                 230                 235                 240 agt gct gag aac tac tcc ctc tat atg tca aga gaa ggt tat act gcc              768
Ser Ala Glu Asn Tyr Ser Leu Tyr Met Ser Arg Glu Gly Tyr Thr Ala
                245                 250                 255 tgg ttc tgt ggt act aac gag gac ttc gcc aag tat gct tca aac att              816
Trp Phe Cys Gly Thr Asn Glu Asp Phe Ala Lys Tyr Ala Ser Asn Ile
            260                 265                 270 aga aag gtt gca gct gat tac aga gaa aag tat gcc ttt gtt ttc ctt              864
Arg Lys Val Ala Ala Asp Tyr Arg Glu Lys Tyr Ala Phe Val Phe Leu
            275                 280                 285 gat act gag caa ttt ggt tcc cat gct act caa cat ctc tta att gag              912
Asp Thr Glu Gln Phe Gly Ser His Ala Thr Gln His Leu Leu Ile Glu
            290                 295                 300 aaa ttc cca ggt ttg gtt atc caa agt gtc aat gtt cca tca att aga              960
Lys Phe Pro Gly Leu Val Ile Gln Ser Val Asn Val Pro Ser Ile Arg
305                 310                 315                 320 tac atg tat ggt cca gct aaa ttc gac tct gtt gag cca tta aag gaa              1008
Tyr Met Tyr Gly Pro Ala Lys Phe Asp Ser Val Glu Pro Leu Lys Glu
                325                 330                 335 ttt atg aag caa gtt tct gaa ggc aag cac gaa ctc agc att aag tct              1056
Phe Met Lys Gln Val Ser Glu Gly Lys His Glu Leu Ser Ile Lys Ser
            340                 345                 350
```

-continued

```
gag cca atc cca gct gag caa tct ggt cca gtc act gtt gtt gtt ggt    1104
Glu Pro Ile Pro Ala Glu Gln Ser Gly Pro Val Thr Val Val Val Gly
        355                 360                 365 aag acc ttc gaa gaa att gtt ttc aga agt gac aag gat gtt ctt ttg    1152
Lys Thr Phe Glu Glu Ile Val Phe Arg Ser Asp Lys Asp Val Leu Leu
    370                 375                 380 gaa atc tat gcc caa tgg tgt gga cac tgt aag aac ctc gag cca atc    1200
Glu Ile Tyr Ala Gln Trp Cys Gly His Cys Lys Asn Leu Glu Pro Ile
385                 390                 395                 400 tac aac caa ctc ggc gaa gag tac aag gac aac gac aag gtt gtg att    1248
Tyr Asn Gln Leu Gly Glu Glu Tyr Lys Asp Asn Asp Lys Val Val Ile
                405                 410                 415 gca aag atc aat gga cca caa aac gat atc cca tat gaa ggt ttc agt    1296
Ala Lys Ile Asn Gly Pro Gln Asn Asp Ile Pro Tyr Glu Gly Phe Ser
            420                 425                 430 cca aga gcc ttc cca act atc ttg ttc gtc aag gcc gga act aga acc    1344
Pro Arg Ala Phe Pro Thr Ile Leu Phe Val Lys Ala Gly Thr Arg Thr
        435                 440                 445 cca att cct tat gat gga aag aga act gtt gag gcc ttc aag gaa ttc    1392
Pro Ile Pro Tyr Asp Gly Lys Arg Thr Val Glu Ala Phe Lys Glu Phe
    450                 455                 460 atc agt gaa cat tct tcc ttc cct caa gaa aag gaa tct cgt gac gaa    1440
Ile Ser Glu His Ser Ser Phe Pro Gln Glu Lys Glu Ser Arg Asp Glu
465                 470                 475                 480 ctc taa                                                            1446
Leu
```

<210> SEQ ID NO 2
<211> LENGTH: 481
<212> TYPE: PRT
<213> ORGANISM: Cryptosporidium parvum

<400> SEQUENCE: 2

```
Met Ile Gly Ile Arg Ser Leu Val Ser Ala Ala Phe Leu Gly Phe Ser
  1               5                  10                  15

Cys Leu Ser Lys Val Val Leu Gly Gly Asp Glu Ala His Phe Ile Ser
             20                  25                  30

Glu His Ile Thr Ser Leu Thr Ser Ser Asn Phe Glu Asp Phe Ile Lys
         35                  40                  45

Ser Lys Glu His Val Ile Val Thr Phe Phe Ala Pro Trp Cys Gly His
     50                  55                  60

Cys Thr Ala Leu Glu Pro Glu Phe Lys Ala Thr Cys Ala Glu Ile Ser
 65                  70                  75                  80

Lys Leu Ser Pro Pro Val His Cys Gly Ser Val Asp Ala Thr Glu Asn
                 85                  90                  95

Met Glu Leu Ala Gln Gln Tyr Gly Val Ser Gly Tyr Pro Thr Ile Lys
            100                 105                 110

Phe Phe Ser Gly Ile Asp Ser Val Gln Asn Tyr Ser Gly Ala Arg Ser
        115                 120                 125

Lys Asp Ala Phe Ile Lys Tyr Ile Lys Lys Leu Thr Gly Pro Ala Val
    130                 135                 140

Gln Val Ala Glu Ser Glu Glu Ala Ile Lys Thr Ile Phe Ala Ser Ser
145                 150                 155                 160

Ser Ser Ala Phe Val Gly Arg Phe Thr Ser Lys Asp Ser Ala Glu Tyr
                165                 170                 175

Ala Val Phe Glu Lys Val Ala Ser Gly His Arg Glu His Asn Tyr Ala
            180                 185                 190
```

-continued

```
Phe Ile Ala Phe Phe Gln Glu Gly Glu Gln Lys Leu Glu Val Leu His
        195                 200                 205
Lys Asp Glu Glu Pro Val Ser Leu Pro Met Pro Lys Thr Val Glu Glu
210                 215                 220
Leu Glu Ala Lys Ile Ser Ile Met Asn Val Pro Leu Phe Ser Ala Ile
225                 230                 235                 240
Ser Ala Glu Asn Tyr Ser Leu Tyr Met Ser Arg Glu Gly Tyr Thr Ala
                245                 250                 255
Trp Phe Cys Gly Thr Asn Glu Asp Phe Ala Lys Tyr Ala Ser Asn Ile
            260                 265                 270
Arg Lys Val Ala Ala Asp Tyr Arg Glu Lys Tyr Ala Phe Val Phe Leu
        275                 280                 285
Asp Thr Glu Gln Phe Gly Ser His Ala Thr Gln His Leu Leu Ile Glu
290                 295                 300
Lys Phe Pro Gly Leu Val Ile Gln Ser Val Asn Val Pro Ser Ile Arg
305                 310                 315                 320
Tyr Met Tyr Gly Pro Ala Lys Phe Asp Ser Val Glu Pro Leu Lys Glu
                325                 330                 335
Phe Met Lys Gln Val Ser Glu Gly Lys His Glu Leu Ser Ile Lys Ser
            340                 345                 350
Glu Pro Ile Pro Ala Glu Gln Ser Gly Pro Val Thr Val Val Gly
        355                 360                 365
Lys Thr Phe Glu Glu Ile Val Phe Arg Ser Asp Lys Asp Val Leu Leu
370                 375                 380
Glu Ile Tyr Ala Gln Trp Cys Gly His Cys Lys Asn Leu Glu Pro Ile
385                 390                 395                 400
Tyr Asn Gln Leu Gly Glu Glu Tyr Lys Asp Asn Asp Lys Val Val Ile
                405                 410                 415
Ala Lys Ile Asn Gly Pro Gln Asn Asp Ile Pro Tyr Glu Gly Phe Ser
            420                 425                 430
Pro Arg Ala Phe Pro Thr Ile Leu Phe Val Lys Ala Gly Thr Arg Thr
        435                 440                 445
Pro Ile Pro Tyr Asp Gly Lys Arg Thr Val Glu Ala Phe Lys Glu Phe
450                 455                 460
Ile Ser Glu His Ser Ser Phe Pro Gln Glu Lys Glu Ser Arg Asp Glu
465                 470                 475                 480
Leu
```

```
<210> SEQ ID NO 3
<211> LENGTH: 32
<212> TYPE: PRT
<213> ORGANISM: Cryptosporidium parvum
<220> FEATURE:
<221> NAME/KEY: PEPTIDE
<222> LOCATION: (1)..(32)
<223> OTHER INFORMATION: 32 amino acid region for C. parvum  protein
      disulfide isomerase (PDI) of Applicants differing
      from Blunt et al. (1996) Gene 181:221-223; GenBank
      Accession No. U48261

<400> SEQUENCE: 3
```

```
Ala Trp Phe Cys Gly Thr Asn Glu Asp Phe Ala Lys Tyr Ala Ser Asn
 1               5                  10                  15
Ile Arg Lys Val Ala Ala Asp Tyr Arg Glu Lys Tyr Ala Phe Val Phe
            20                  25                  30
```

```
<210> SEQ ID NO 4
```

```
<211> LENGTH: 41
<212> TYPE: PRT
<213> ORGANISM: Cryptosporidium parvum
<220> FEATURE:
<221> NAME/KEY: PEPTIDE
<222> LOCATION: (1)..(41)
<223> OTHER INFORMATION: positions 250-290 of C. parvum protein
      disulfide isomerase (PDI) according to Blunt et al. (1996)
      Gene 181:221-223; GenBank Accession No. U48261
<220> FEATURE:
<221> NAME/KEY: PEPTIDE
<222> LOCATION: (7)..(38)
<223> OTHER INFORMATION: 32 amino acid region of C. parvum protein
      disulfide isomerase (PDI) of Blunt et al. that
      differs from that of Applicant PDI

<400> SEQUENCE: 4

Ser Arg Glu Gly Tyr Thr Pro Gly Ser Val Val Leu Thr Arg Thr Ser
 1               5                  10                  15

Pro Ser Met Leu Gln Thr Leu Glu Arg Leu Gln Leu Ile Thr Glu Lys
            20                  25                  30

Ser Met Pro Leu Phe Ser Leu Asp Thr
        35                  40

<210> SEQ ID NO 5
<211> LENGTH: 41
<212> TYPE: PRT
<213> ORGANISM: Cryptosporidium parvum
<220> FEATURE:
<221> NAME/KEY: PEPTIDE
<222> LOCATION: (1)..(41)
<223> OTHER INFORMATION: positions 250-290 (numbering convention used by
      Blunt et al.) of C. parvum protein disulfide
      isomerase (PDI) of the Applicants
<220> FEATURE:
<221> NAME/KEY: PEPTIDE
<222> LOCATION: (7)..(38)
<223> OTHER INFORMATION: 32 amino acid region of C. parvum protein
      disulfide isomerase (PDI) from Applicants that
      differs from Blunt et al. PDI

<400> SEQUENCE: 5

Ser Arg Glu Gly Tyr Thr Ala Trp Phe Cys Gly Thr Asn Glu Asp Phe
 1               5                  10                  15

Ala Lys Tyr Ala Ser Asn Ile Arg Lys Val Ala Ala Asp Tyr Arg Glu
            20                  25                  30

Lys Tyr Ala Phe Val Phe Leu Asp Thr
        35                  40

<210> SEQ ID NO 6
<211> LENGTH: 23
<212> TYPE: DNA
<213> ORGANISM: Cryptosporidium parvum
<220> FEATURE:
<223> OTHER INFORMATION: primer A

<400> SEQUENCE: 6
gtaaaacgac ggccagtgaa ttg                                          23

<210> SEQ ID NO 7
<211> LENGTH: 54
<212> TYPE: DNA
<213> ORGANISM: Cryptosporidium parvum
<220> FEATURE:
<223> OTHER INFORMATION: primer B

<400> SEQUENCE: 7
acccgttttt ttggatggag tgaaacgatg atcggaattc gtagcttggt ttca        54
```

```
<210> SEQ ID NO 8
<211> LENGTH: 89
<212> TYPE: DNA
<213> ORGANISM: Cryptosporidium parvum
<220> FEATURE:
<223> OTHER INFORMATION: primer C

<400> SEQUENCE: 8
gtgataaact accgcattaa agcttatcga tgataagctg tcaattagtg atggtgatgg      60
tgatggagtt cgtcacgaga ttccttttc                                       89

<210> SEQ ID NO 9
<211> LENGTH: 20
<212> TYPE: DNA
<213> ORGANISM: Cryptosporidium parvum
<220> FEATURE:
<223> OTHER INFORMATION: primer D

<400> SEQUENCE: 9
tccaaggtag tcttgggtgg                                                  20

<210> SEQ ID NO 10
<211> LENGTH: 20
<212> TYPE: DNA
<213> ORGANISM: Cryptosporidium parvum
<220> FEATURE:
<223> OTHER INFORMATION: primer E

<400> SEQUENCE: 10
aagctctctc ccccagtaca                                                  20

<210> SEQ ID NO 11
<211> LENGTH: 20
<212> TYPE: DNA
<213> ORGANISM: Cryptosporidium parvum
<220> FEATURE:
<223> OTHER INFORMATION: primer F

<400> SEQUENCE: 11
gcagtccaag ttgctgaatc                                                  20

<210> SEQ ID NO 12
<211> LENGTH: 20
<212> TYPE: DNA
<213> ORGANISM: Cryptosporidium parvum
<220> FEATURE:
<223> OTHER INFORMATION: primer G

<400> SEQUENCE: 12
ctcgaggtat tacacaagga                                                  20

<210> SEQ ID NO 13
<211> LENGTH: 20
<212> TYPE: DNA
<213> ORGANISM: Cryptosporidium parvum
<220> FEATURE:
<223> OTHER INFORMATION: primer H

<400> SEQUENCE: 13
ccaagtatgc ttcaaacatt                                                  20

<210> SEQ ID NO 14
<211> LENGTH: 20
<212> TYPE: DNA
```

```
<213> ORGANISM: Cryptosporidium parvum
<220> FEATURE:
<223> OTHER INFORMATION: primer I

<400> SEQUENCE: 14
ttcgactctg ttgagccatt                                                    20

<210> SEQ ID NO 15
<211> LENGTH: 21
<212> TYPE: DNA
<213> ORGANISM: Cryptosporidium parvum
<220> FEATURE:
<223> OTHER INFORMATION: primer J

<400> SEQUENCE: 15
tgtggacact gtaagaacct c                                                  21

<210> SEQ ID NO 16
<211> LENGTH: 18
<212> TYPE: DNA
<213> ORGANISM: Cryptosporidium parvum
<220> FEATURE:
<223> OTHER INFORMATION: primer K

<400> SEQUENCE: 16
gaggatgacg atgagcgc                                                      18

<210> SEQ ID NO 17
<211> LENGTH: 21
<212> TYPE: DNA
<213> ORGANISM: Cryptosporidium parvum
<220> FEATURE:
<223> OTHER INFORMATION: primer L

<400> SEQUENCE: 17
gcaactctct actgtttctc c                                                  21

<210> SEQ ID NO 18
<211> LENGTH: 20
<212> TYPE: DNA
<213> ORGANISM: Cryptosporidium parvum
<220> FEATURE:
<223> OTHER INFORMATION: primer M

<400> SEQUENCE: 18
tcgctgccca accagccatg                                                    20

<210> SEQ ID NO 19
<211> LENGTH: 75
<212> TYPE: DNA
<213> ORGANISM: Cryptosporidium parvum
<220> FEATURE:
<223> OTHER INFORMATION: primer N

<400> SEQUENCE: 19
gtgataaact accgcattaa agcttatcga tgataagctg tcaattagtg atggtgatgg        60
tgatgacaat ccctg                                                         75
```